(12) United States Patent
Urbanski et al.

(10) Patent No.: US 10,207,119 B2
(45) Date of Patent: Feb. 19, 2019

(54) IMPLANTABLE DEVICES WITH THIN FILM FEEDTHROUGH

(71) Applicant: PACESETTER, INC., Sylmar, CA (US)

(72) Inventors: Jeffrey Urbanski, Frisco, TX (US);
Theodore Alfonso, Frisco, TX (US);
John R. Gonzalez, McKinney, TX (US)

(73) Assignee: PACESETTER, INC., Sylmar, CA (US)

( * ) Notice: Subject to any disclaimer, the term of this patent is extended or adjusted under 35 U.S.C. 154(b) by 106 days.

(21) Appl. No.: 15/465,423

(22) Filed: Mar. 21, 2017

(65) Prior Publication Data

US 2018/0169417 A1    Jun. 21, 2018

Related U.S. Application Data

(60) Provisional application No. 62/436,881, filed on Dec. 20, 2016.

(51) Int. Cl.
| | | |
|---|---|---|
| *A61N 1/00* | (2006.01) | |
| *A61N 1/375* | (2006.01) | |
| *H05K 5/00* | (2006.01) | |
| A61N 1/372 | (2006.01) | |
| H05K 3/28 | (2006.01) | |
| H05K 1/03 | (2006.01) | |

(52) U.S. Cl.
CPC ......... *A61N 1/3754* (2013.01); *H05K 5/0095* (2013.01); *A61N 1/372* (2013.01); *A61N 1/37512* (2017.08); *H05K 1/0306* (2013.01); *H05K 3/28* (2013.01)

(58) Field of Classification Search
CPC .. A61N 1/372; A61N 1/3754; A61N 1/37512; H05K 1/0306; H05K 3/28; H05K 5/0095
See application file for complete search history.

(56) References Cited

U.S. PATENT DOCUMENTS

| | | | | |
|---|---|---|---|---|
| 6,564,106 B2* | 5/2003 | Guck | ....................... | A61N 1/08 600/373 |
| 2002/0072778 A1* | 6/2002 | Guck | ....................... | A61N 1/08 607/36 |
| 2011/0144415 A1* | 6/2011 | Hellmuth | ............. | H04R 25/606 600/25 |

* cited by examiner

*Primary Examiner* — George Manuel

(57) ABSTRACT

Implementations described and claimed herein provide implantable electronic devices having a thin film feedthrough and methods of manufacturing the same. In one implementation, an implantable electronic device includes a housing enclosing one or more internal electronic components within a hermetic environment. A feedthrough port is defined in a wall of the housing. A thin film feedthrough has a feedthrough body extending through the feedthrough port. The feedthrough body provides one or more electrical pathways between external contacts and internal contacts. The external contacts are disposed outside the hermetic environment, and the internal contacts are electrically connected to the one or more internal electronic components at an internal connection junction. A hermetic junction is disposed in the feedthrough port isolating the thin film feedthrough from the housing.

20 Claims, 28 Drawing Sheets

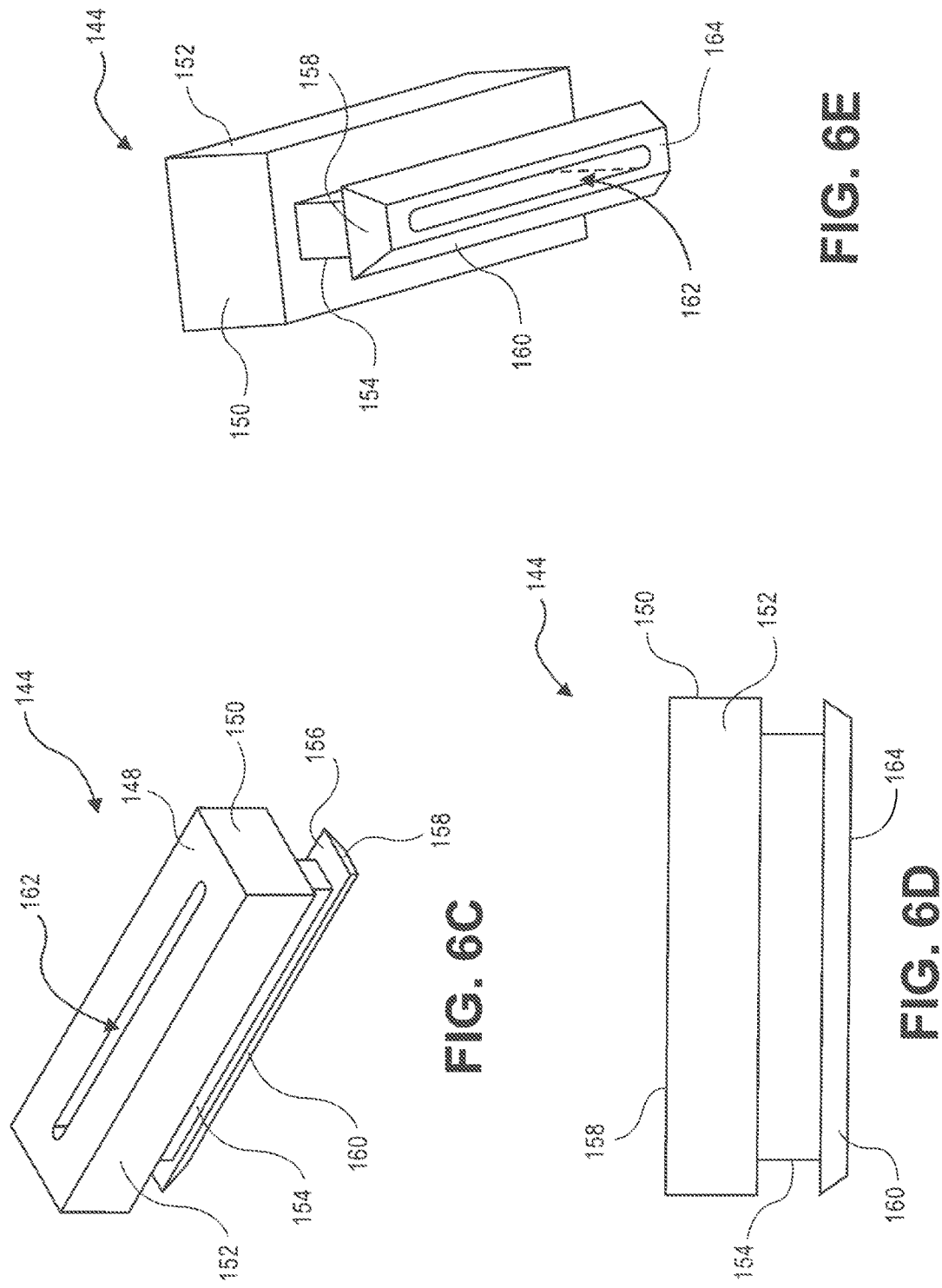

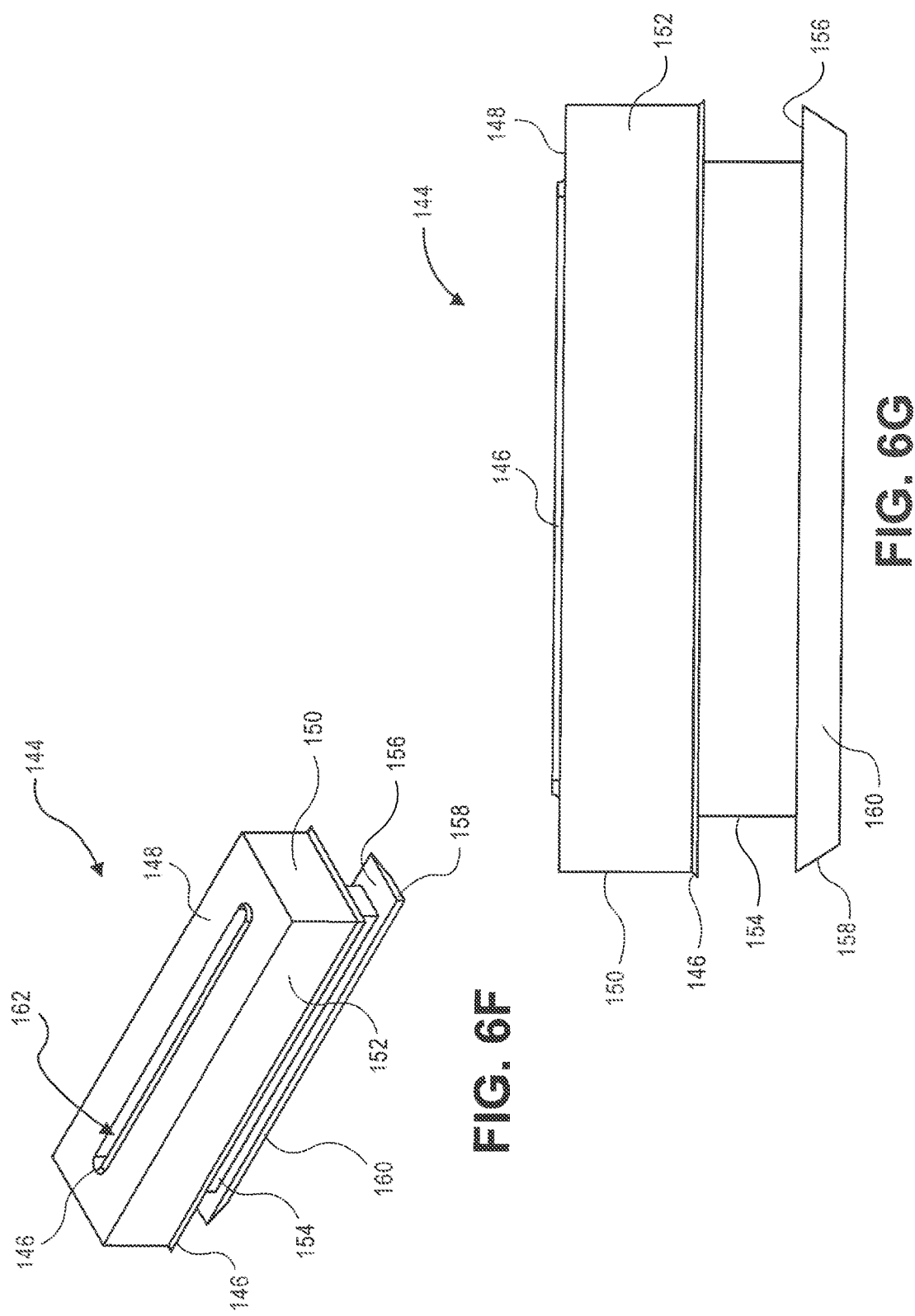

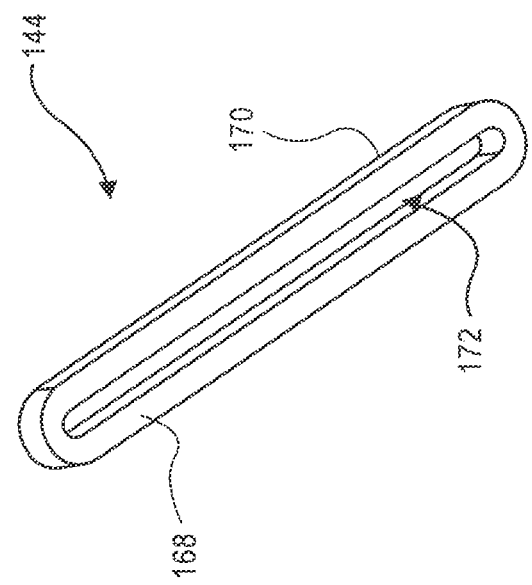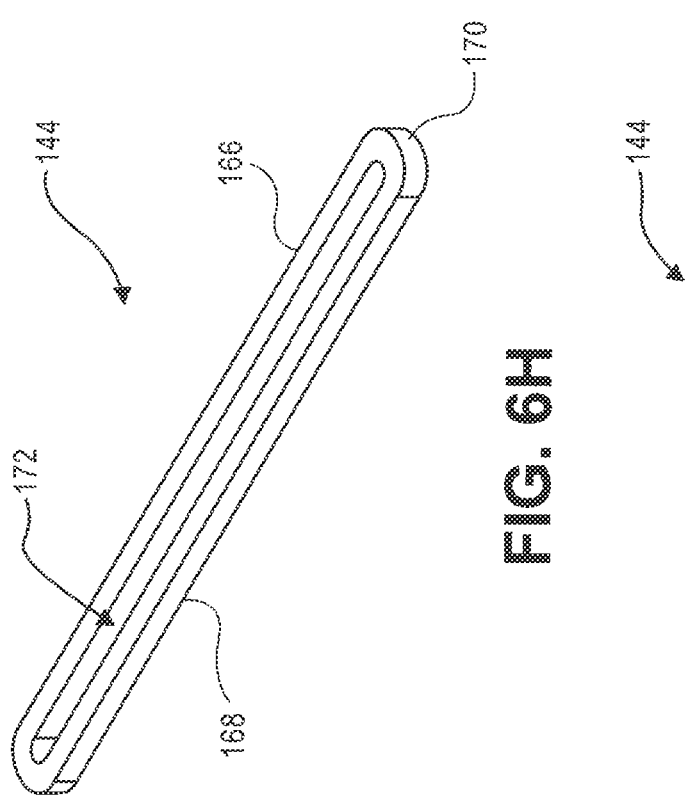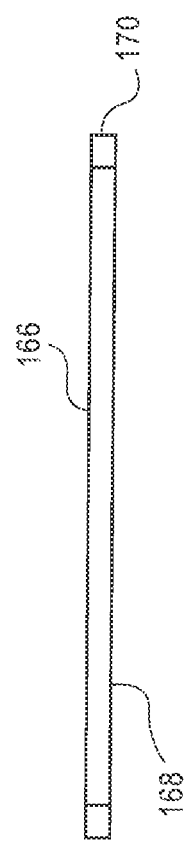

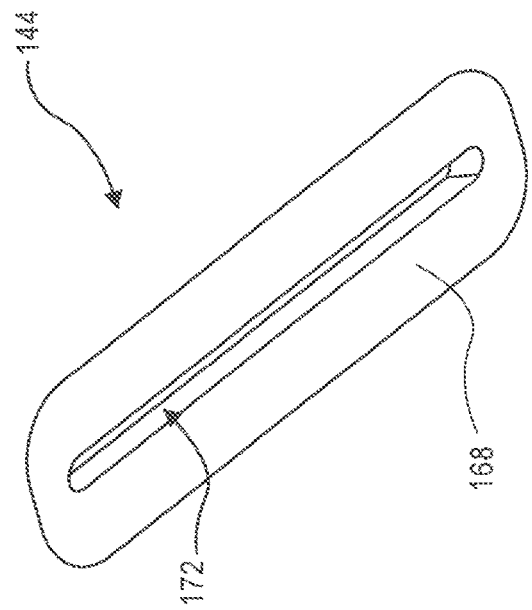
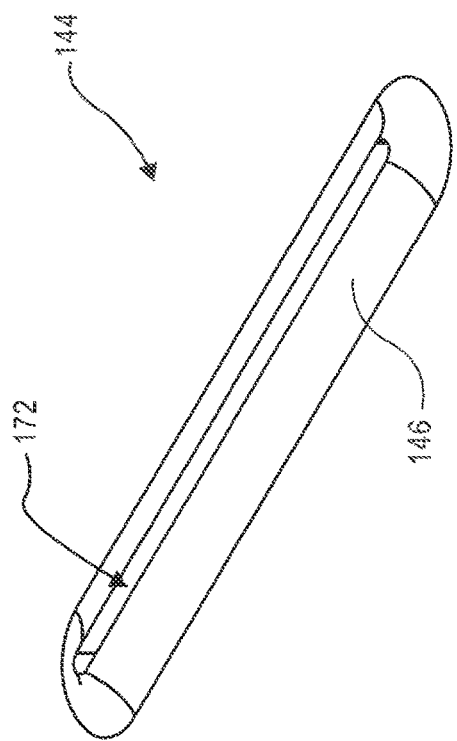
FIG. 6M
FIG. 6K
FIG. 6L

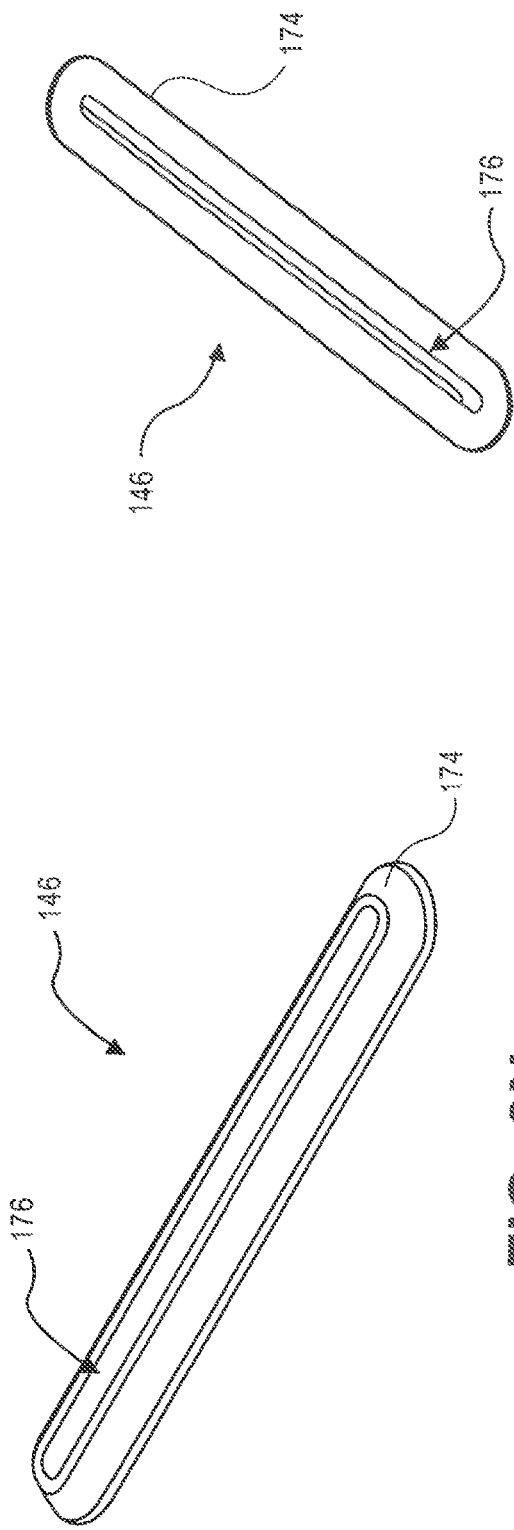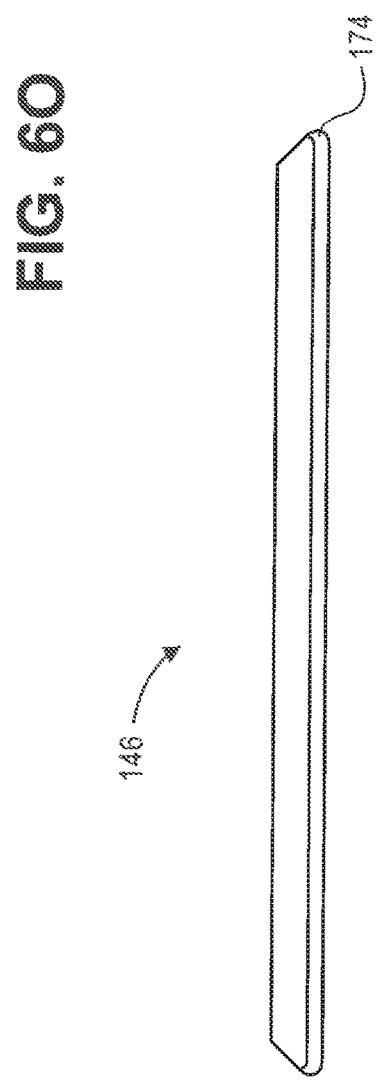

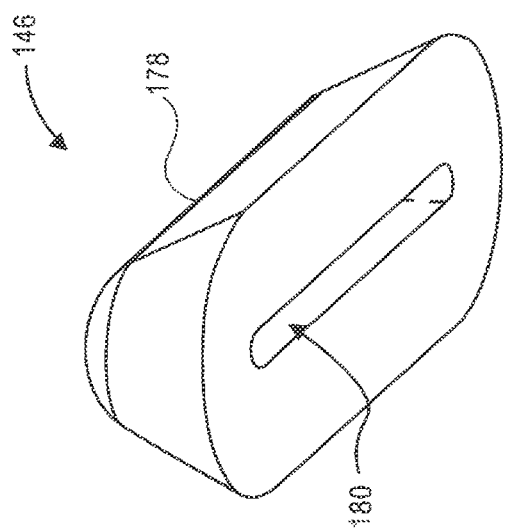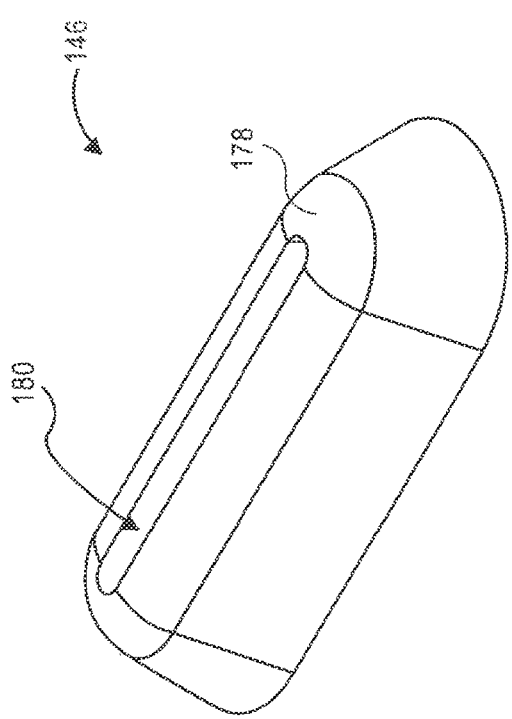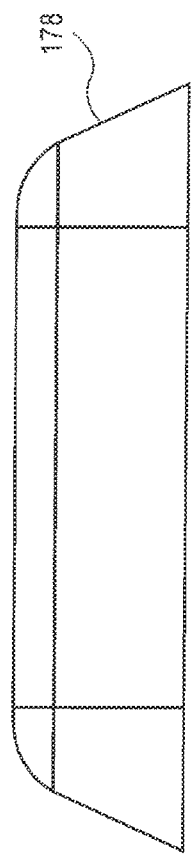

IMPLANTABLE DEVICES WITH THIN FILM FEEDTHROUGH

CROSS REFERENCE TO RELATED APPLICATIONS

This application claims the benefit of U.S. Provisional Patent Application Ser. No. 62/436,881, filed Dec. 20, 2016, which is incorporated herein in its entirety.

TECHNICAL FIELD

Aspects of the present disclosure relate to electronic devices implantable in a patient for treatment delivery and/or monitoring and more particularly to implantable electronic devices having a thin film feedthrough to transmit one or more discrete electrical signals between internal electronics and external contacts.

BACKGROUND OF THE INVENTION

Treatment and/or monitoring of various types of medical conditions may utilize implantable electronic devices (IEDs). Such IEDs may include, without limitation, implantable pulse generators (IPGs), implantable cardiac monitors (ICMs), and the like. IPGs generate an electrical current for delivery to a target location of a patient for treatment. For example, pacemakers and implantable cardioverter defibrillators (ICDs) drive an electrical current into cardiac tissue to treat various cardia conditions. Similarly, neuromodulators or neurostimulators deliver electrical current into particular regions of the spinal cord or other body system to manage chronic pain and/or actuate or otherwise control an aspect of that body system. ICMs, on the other hand, are generally used to monitor heart function and/or other electrical signals without administering electrotherapy.

IEDs typically include a housing that isolates internal electronic components from tissues and bodily fluids surrounding the IED. Discrete electrical signals are passed through the housing along an electrical pathway between the internal electronic components within a hermetic environment and external electronic components outside the hermetic environment. Conventionally, the electronic pathway is a feedthrough comprised of conductive elements assembled within a dielectric material through a process providing a hermetic seal between the dielectric materials and the conductive elements.

Such conventional feedthrough assembly procedures are often cumbersome, complex, and unaccommodating for disparate configurations and/or treatment applications. For example, a number of conductive elements may range from a single conductor to hundreds, with the inputs and outputs needed for passing each conductor through varying depending on the electrical current and/or sensitivity parameters of the treatment application. Further, a size, shape, material, and/or location of each of the conductors is often dependent on an input/output from the internal electrical components, and connection methods for each end of the conductors varies based on whether the connection is within or outside of the hermetic environment.

The hermetic seal of the feedthroughs are commonly created using a high temperature reflow, brazing, or sintering process, where the choice of material for the feedthrough must be carefully selected to provide sufficient thermal stability during the process. This material selection thus limits the ability to adapt aspects of the feedthrough to accommodate various configurations and/or treatment applications. With the complexity and number of input/outputs for IEDs continuing to grow with the enhancement of therapeutic and diagnostic capabilities, there is a need in the art for a customizable IED that is less expensive and labor intensive to manufacture. It is with these observations in mind, among others, that various aspects of the present disclosure were conceived and developed.

SUMMARY

Implementations described and claimed herein address the foregoing problems, among others, by providing implantable electronic devices having a thin film feedthrough and methods of manufacturing the same. In one implementation, an implantable electronic device includes a housing enclosing one or more internal electronic components within a hermetic environment. A feedthrough port is defined in a wall of the housing. A thin film feedthrough has a feedthrough body extending through the feedthrough port. The feedthrough body provides one or more electrical pathways between external contacts and internal contacts. The external contacts are disposed outside the hermetic environment, and the internal contacts are electrically connected to the one or more internal electronic components at an internal connection junction. A hermetic junction is disposed in the feedthrough port isolating the thin film feedthrough from the housing.

Other implementations are also described and recited herein. Further, while multiple implementations are disclosed, still other implementations of the presently disclosed technology will become apparent to those skilled in the art from the following detailed description, which shows and describes illustrative implementations of the presently disclosed technology. As will be realized, the presently disclosed technology is capable of modifications in various aspects, all without departing from the spirit and scope of the presently disclosed technology. Accordingly, the drawings and detailed description are to be regarded as illustrative in nature and not limiting.

BRIEF DESCRIPTION OF THE DRAWINGS

FIGS. 6C-6E illustrate detailed top perspective, side, and bottom perspective views, respectively, of an example LCP flange for the hermetic junction.

FIGS. 6F-6G illustrate detailed top perspective and side views, respectively, of the LCP flange of FIGS. 6C-6E following sealing.

FIGS. 6H-6J show detailed top perspective, side, and bottom perspective views, respectively, of an example flange ring for the hermetic junction, prior to sealing.

FIGS. 6K-6M depict detailed top perspective, side, and bottom perspective views, respectively, of the flange ring of FIGS. 6H-6J after sealing.

FIGS. 6N-6P show detailed top perspective, side, and bottom perspective views, respectively, of an example glass bead for the hermetic junction, prior to annealing.

FIGS. 6Q-6S illustrate detailed top perspective, side, and bottom perspective views, respectively, of an example hermetic epoxy seal for the hermetic junction.

DETAILED DESCRIPTION

Figure 1:
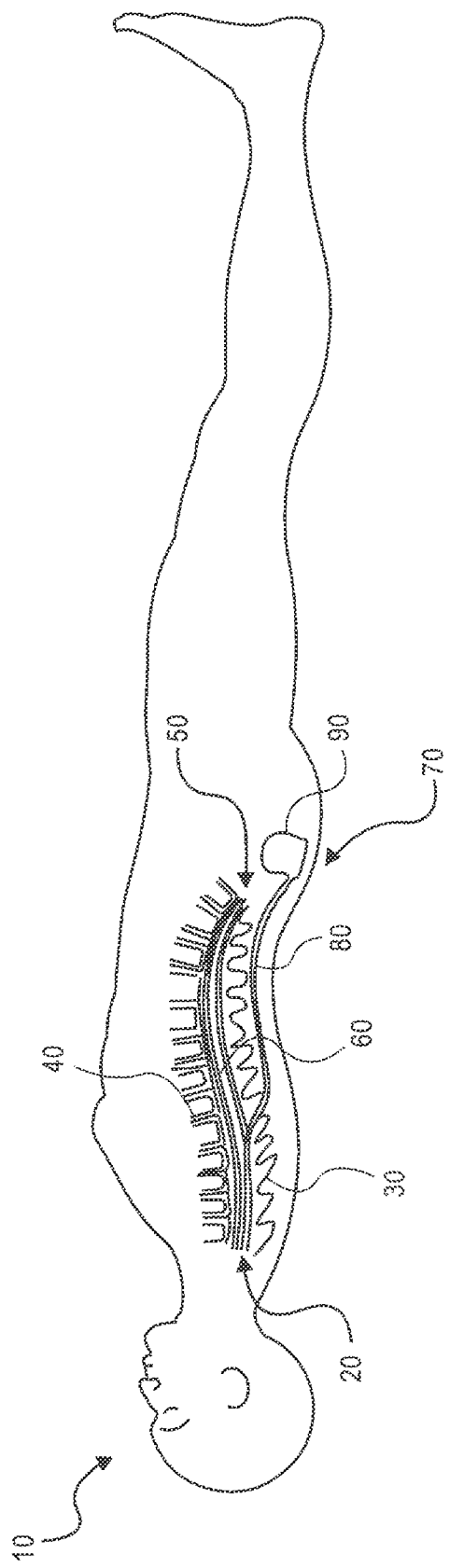
FIG. 1 shows a patient with an example implantable electronic system having an implantable electronic device (IED) in the form of an implantable pulse generator (IPG) configured to deliver an electrical current to the spinal cord via a lead for Spinal Cord Stimulation (SCS), the IPG including a thin film feedthrough connecting the lead to internal electrical components within a hermetic environment of a housing of the IPG.

Aspects of the present disclosure involve implantable electronic devices (IEDs) having a thin film feedthrough and methods of manufacturing the same. Generally, one or more thin film feedthroughs may each extend through a corresponding feedthrough port in a housing to directly transmit discrete electronic signals between internal electronic components disposed within a hermetic environment enclosed within the housing and external contacts disposed outside the hermetic environment. A hermetic junction hermetically seals the feedthrough port isolating the hermetic environment from surrounding patient tissue and fluid. The hermetic junction may be provided, for example, by the application of a sealant, such as an epoxy, annealed glass, or polymer, which forms a contiguous bond and isolates the hermetic environment.

In one aspect, the thin film feedthrough is fabricated using one or more multilayer laminations providing customized conductive pathways. The spacing of the conductive pathways may be compressed, thereby reducing a size and geometry of the thin film feedthrough and accordingly a size of the feedthrough port and by extension the IED. The smaller size and geometry of the thin film feedthrough permits customization of the IED. The conductive pathways may be directly routed from the internal electronic components to the external contacts with each conductive pathway remaining fully insulated between connection junctions. Moreover, a size and configuration of such connection junctions may be independent of feedthrough geometry, permitting further customization of the IED.

Thus, the presently disclosed technology provides flexibility in manufacturing an IED with a thin film feedthrough customized for a selected input/output configuration while minimizing installation cost and complexity and minimizing a footprint of the thin film feedthrough as well as of the IED as a whole. This reduced footprint minimizes the invasiveness and risk of trauma to the patient during deployment.

As described herein, the IED may be an implantable pulse generator (IPG), an implantable cardiac monitor (ICM), or the like. An IPG administers electrotherapy or other neurostimulation via an implantable lead having a connector assembly at a proximal end and a stimulation assembly at a distal end. The IPG includes a housing enclosing internal electrical components, such as a battery, hybrid, and/or the like, within a hermetic environment. The internal electrical components are electrically connected to the connector assembly of the implantable lead using a thin film feedthrough. More particularly, the thin film feedthrough includes a header connector assembly connected to an internal connector assembly via a feedthrough body. The header connector assembly is electrically connected to the connector assembly of the implantable lead at an external connection Junction within a header. The feedthrough body extends through a feedthrough port in the housing into the hermetic environment where the internal connector assembly connects to the internal electrical components at an internal connection junction. The feedthrough port is hermetically sealed with a hermetic junction, which may include a flange. The thin film feedthrough thus creates an electrical connection between the internal electrical components and the stimulation assembly of the implantable lead to deliver electrical current to a target location within a patient. Similarly, electrical signals originating in the target location can travel via the implantable lead and/or thin film feedthrough for sensing by the IPG.

It will be appreciated that while many of the example implementations described herein reference IEDs in the form of IPGs, the presently disclosed technology is applicable to other IEDs and may be customized accordingly. For example, an ICM is similar to the IPG, with a main distinction being that the ICM does not attach to an implantable lead and simply monitors electrical signals without administering therapy.

Additionally, an IED fabricated as an IPG may be configured according to a selected dielectric use for treating and/or monitoring a patient. Such dielectric uses may include, without limitation, spinal cord stimulation (SCS), deep brain stimulation (DBS), catheter ablation, cardiac rhythm management (CRM), occipital nerve stimulation (ONS), peripheral nerve stimulation (PNS), electrophysiology (EP), atrial fibrillation (AF), vagus nerve, and the like. To begin a detailed description of an example of an implantable electronic system having an IPG with a thin film feedthrough formed and deployed for SCS treatment, reference is made to FIG. 1. It will be appreciated that while FIG. 1 references SCS treatment, the presently disclosed technology is applicable to IPGs that are customized for other dielectric uses.

Turning to FIG. 1, a patient 10 is treated for a medical condition through the application of electrical stimulation. In the example implementation shown in FIG. 1, the patient 10 is treated for chronic pain through SCS. In the vertebrate spinal column of the patient 10, the epidural space 20 is positioned at the outermost part of the spinal canal formed by vertebrae 40, which have spinous process 30 projecting therefrom and providing a point of attachment for muscles and ligaments of the patient 10. Ligamentum flavum 50 connect the laminae of adjacent vertebrae 40. The lamina covers the spinal canal, which encloses and protects the spinal cord 60.

In one implementation, an implantable electronic system 70 includes an implantable lead 80 positioned at a target location in the epidural space 20 to drive an electrical current from an IPG 90 into particular regions of the spinal cord 60 of the patient 10 to induce paresthesia. The implantable lead 80 lead may be formed as a percutaneous lead or a paddle lead and deployed into the target location in the epidural space 20 accordingly. As described herein, the footprint of the implantable electronic system 70 within the patient 10 is minimized by customizing the IPG 90 with a thin film feedthrough.

Figure 2:
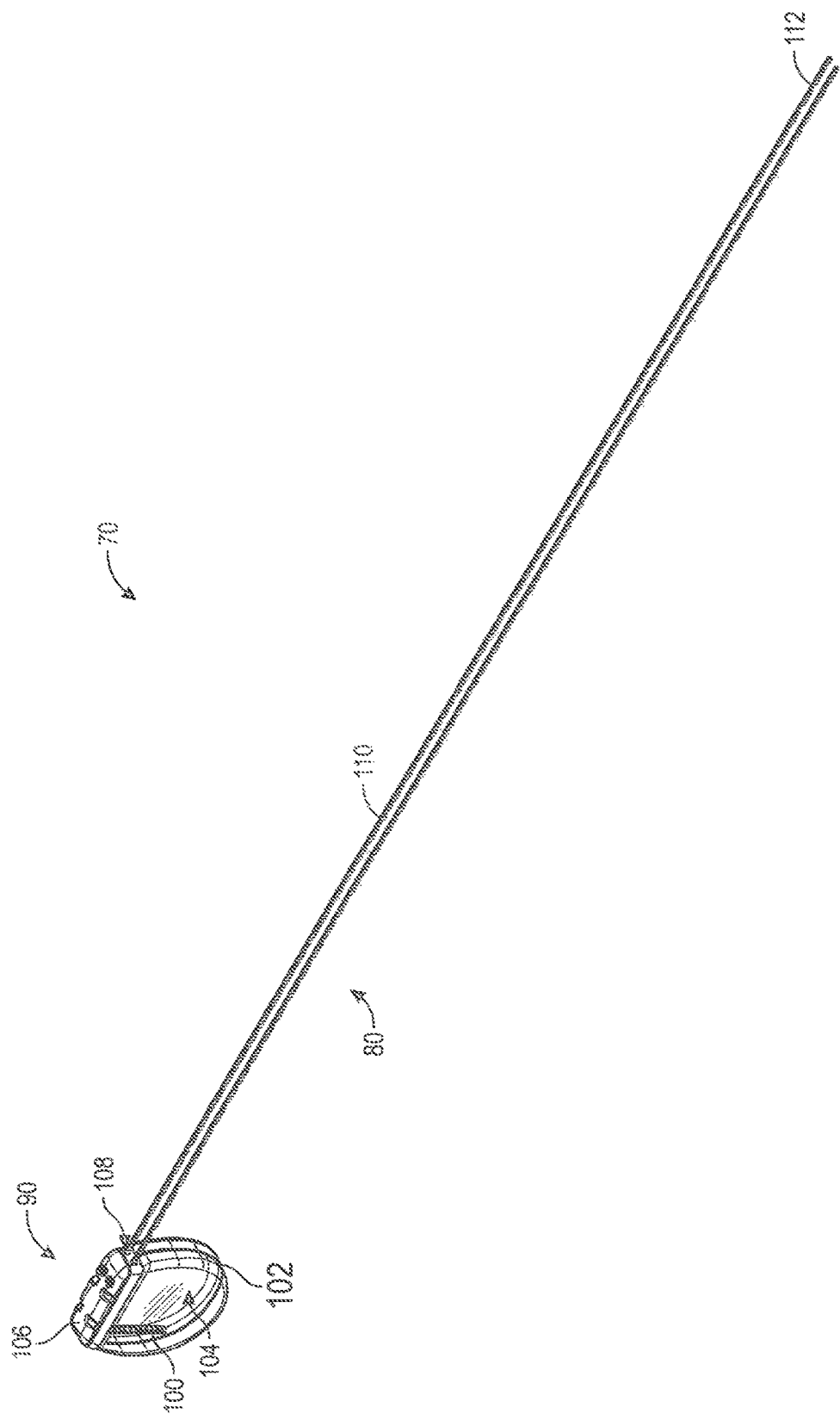
FIG. 2 is a perspective view of an implantable electronic system with an IED having a thin film feedthrough. A housing of the IED is shown transparent for clarity.
Figure 3:
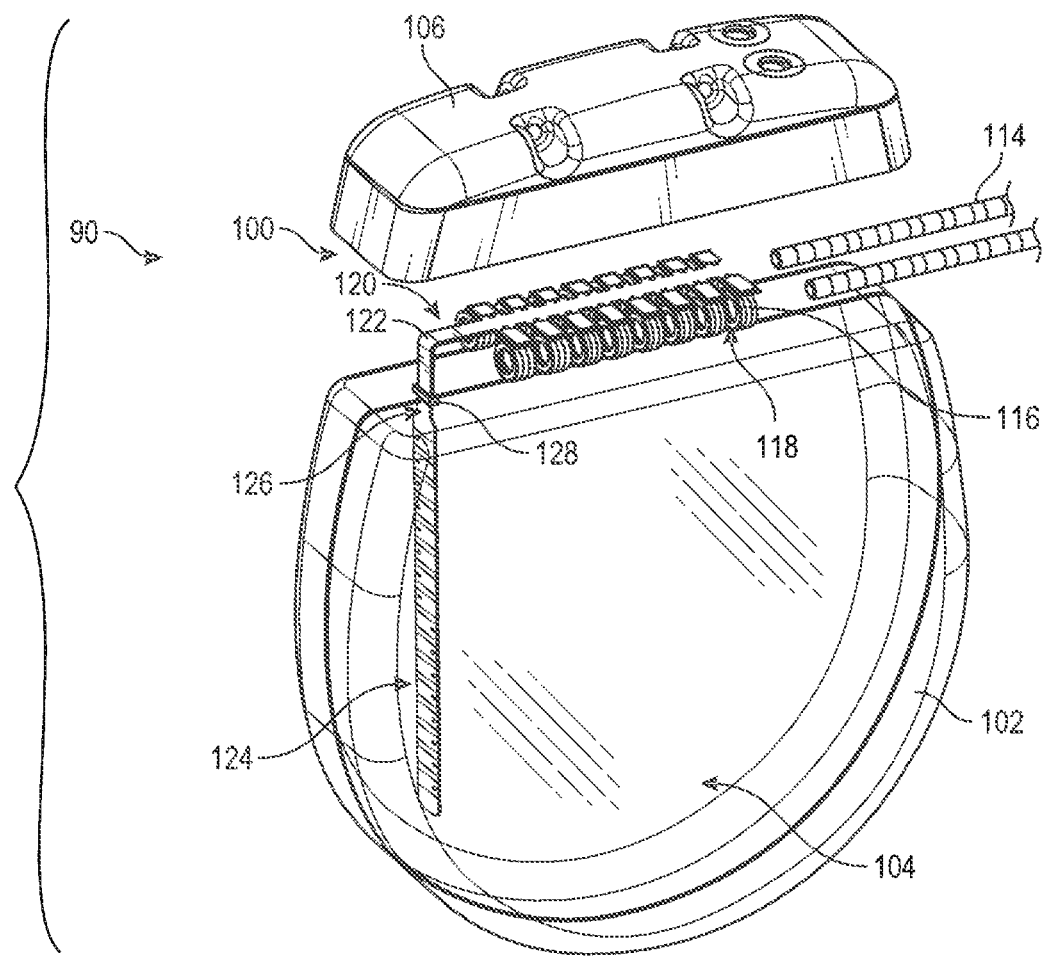
FIG. 3 is a detailed proximal perspective view of the IED of FIG. 2 with a header cover shown disconnected from a housing, a hermetic junction of the thin film feedthrough comprising a liquid crystal polymer (LCP) flange.

To continue a detailed description of an example implantable electronic system 70 with the IPG 90 including a thin film feedthrough 100, reference is made to FIGS. 2-3. In one implementation, the IPG 90 includes a housing 102 enclosing a hermetic environment 104 isolated from tissue and body fluid of the anatomy of the patient 10. The isolation of the hermetic environment 104 prevents any internal short circuit, while protecting against the intrusion of bodily fluids.

In one implementation, a header includes a header cover 106 enclosing a connection junction between the thin film feedthrough 100 and the implantable lead 80. The header cover 106 has one or more lead openings 108 defined therein through which one or more implantable leads 80 extend. More particularly, in one implementation, the one or more implantable leads 80 each include a lead body 110 extending between a simulation assembly 112 disposed at a distal end and a connector assembly 114 disposed at a proximal end. The lead body 110 extends through a corresponding lead opening 108 for connection with the thin film feedthrough 100 within the header. An adhesive, such as a silicone adhesive, may be deployed within the header to mount and protect the components disposed within the header.

The connector assembly 114 is configured to direct electrical current from the IPG 90 via the lead body 110 to the stimulation assembly 112, which delivers the electrical current to the target location in the patient 10. The header may include one or more ball seals 116 each having a ball seal opening 118 configured to receive the proximal end of a corresponding implantable lead 80. The ball seals 116 electrically connect the connector assembly 114 of the implantable lead 80 with a header connector assembly 120 of the thin film feedthrough 100. The header connector assembly 120 is directly connected to an internal connection assembly 124 deployed within the hermetic environment 104 via a feedthrough body 122, thereby communicating electrical signals between the internal electrical components of the IPG 90, such as a battery, hybrid, and/or the like, and the implantable lead 80. The feedthrough body 122 extends through a feedthrough port 126 defined in the housing 102 into the hermetic environment 104. To isolate and seal the hermetic environment 104 from the outside, the thin film feedthrough 100 includes a hermetic junction 128 deployed within the feedthrough port 126. The hermetic junction 128 may include a flange made from liquid crystal polymer (LCP), metal, glass, and/or otherwise through the application of a sealant, such as an epoxy, annealed glass, or polymer, which forms a contiguous bond and isolates the hermetic environment 104.

As described herein, the thin film feedthrough 100 having a hermetic junction 128 reduces a footprint, complexity, and manufacturing cost of the IPG 90, while enabling increased channels having smaller and efficient connections between the internal electronic components within the hermetic environment 104 and external electronics, such as the implantable lead 80. Overall, the thin film feedthrough 100 minimizes an otherwise complex fabrication process and facilitates rapid production of multiple disparate configurations.

Figure 4:
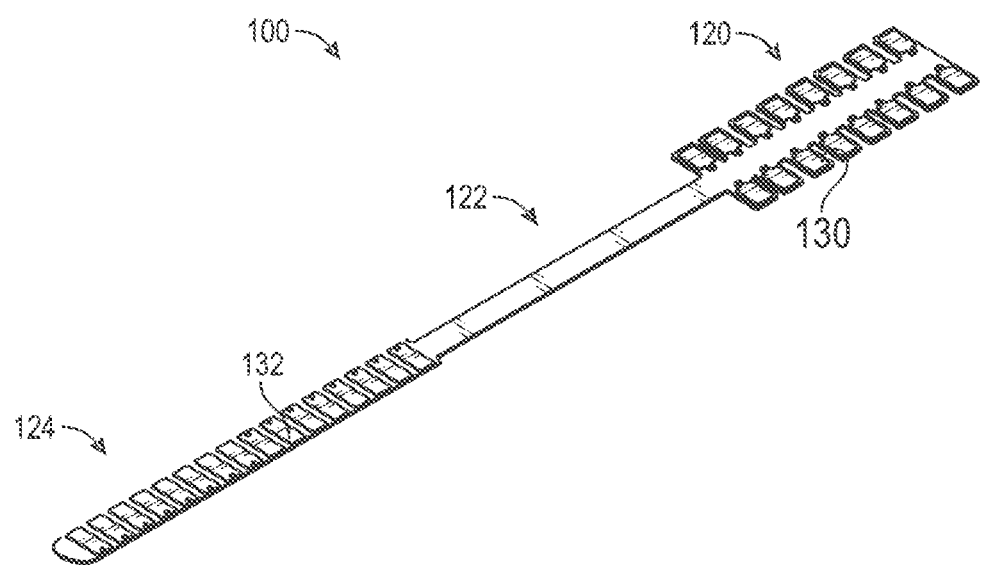
FIG. 4 is a perspective view of an example thin film feedthrough.
Figure 5:
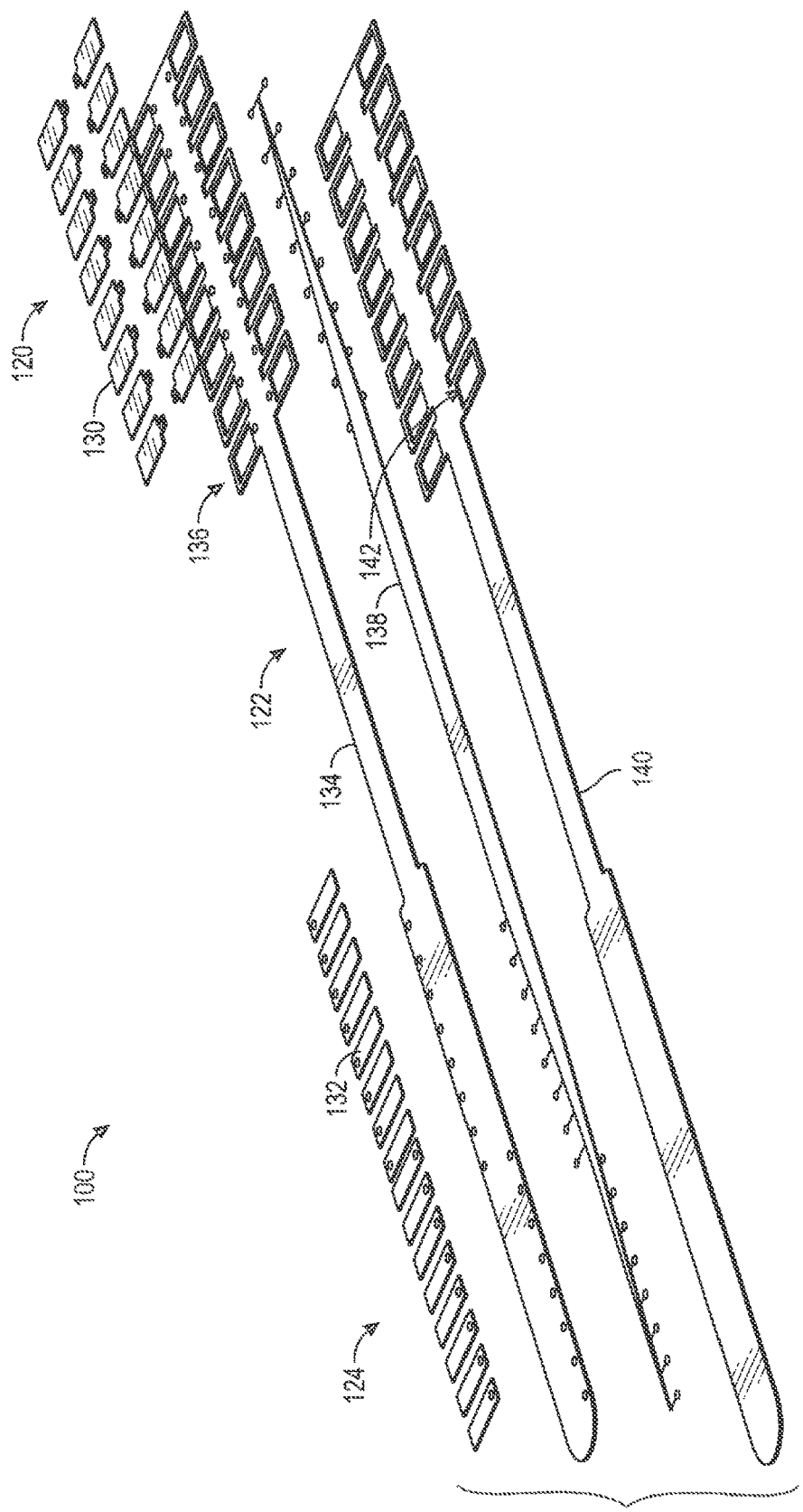
FIG. 5 is an exploded view of the thin film feedthrough of FIG. 4.

Turning to FIGS. 4-5, an example of the thin film feedthrough 100 fabricated for a selected configuration is shown. The thin film feedthrough 100 may be fabricated using a plated through hole integration process, a sequential metal integration process, a glass feedthrough process, and/or the like. In one implementation, the thin film feedthrough 100 includes the header connection assembly 120 with a plurality of external electrode contacts 130. Each of the external electrode contacts 130 is in electrical communication with a corresponding internal electrode contact 132 of the internal connection assembly 124 via the feedthrough body 122.

The thin film feedthrough 100 may include any number of external electrode contacts 130 and internal electrode contacts 132 depending on the application of the implantable electrical system 70. For example, as shown in FIGS. 3-4, in one particular example, the thin film feedthrough 100 provides a single sixteen channel feedthrough, with the header connection assembly 120 having two sets of eight external electrode contacts 130 and the internal connection assembly 124 having a line of sixteen internal electrode contacts 132 corresponding thereto. The number and arrangement of the ball seals 116 may mirror the number and arrangement of the external electrode contacts 130 with each of the ball seals 116 electrically connecting one of the external electrode contacts 130 with a corresponding contact of the connector assembly 114 of the implantable lead 80.

Referring to FIG. 5, in one implementation, the thin film feedthrough 100 may be manufactured by providing a substrate 140, for example, made from an insulating material, including, without limitation, polyimide, organic thermoplastic polymer (e.g., Polyether ether ketone (PEEK)), liquid crystal polymer (LCP), flexible glass, flexible ceramic, rigid ceramic, and/or other insulating materials. The substrate 140 may be flexible, non-flexible (e.g., rigid), a combination of flexible and non-flexible, or transitionally stiff (e.g., transitioning or otherwise varying in stiffness from flexible to rigid along a length of the substrate 140). One or more contact openings 142 and/or 136 are defined in the substrate 140 and/or an passivation layer 134 made from insulating material through which one of the corresponding external electrode contacts 130 may electrically connect to one of the ball seals 116 and thereby a corresponding contact of the connector assembly 114 of the implantable lead 80. In one implementation, a profile of the insulator 140 defined transverse to the length of the substrate 140 is shaped according to the application of the implantable electrical system 70, for example, to facilitate connection to the connector assembly 114 at an external connection junction.

An interconnect 138 is fabricated on the substrate 140 with a layer of conductive traces. The layer of conductive traces defines a trace pattern. In one implementation, the trace pattern includes one or more header connection end traces, internal connection end traces, and body traces. The header connection end traces may be fabricated on the inner surface of the insulator 140 at the header connector assembly 120 to electrically connect the external electrode contacts 130, and the internal connection end traces may be fabricated on the inner surface of the insulator 140 at the internal connection assembly 124 to electrically connect the internal electrode contacts 132. The body traces connect the header connection end traces to the internal connection end traces to provide direct electrical pathways between the internal connection assembly 124 and the header connector assembly 120.

In one implementation, the interconnect 138 is fabricated on the inner surface of the insulator 140 using biocompatible metallization. The biocompatible metallization may include, without limitation, metal deposition, foil attachment (e.g., laminated foils), conductive printing, and/or the like using one or more metals. The trace pattern may be defined using resist printing, ablation (e.g., laser ablation), etching, conductive printing, insulative impregnation, insulative implantation, and/or the like. For example, the layer of conductive traces may be fabricated using a fully biocompatible deposited or etched foil metal scheme. The metals may include, without limitation, Palladium (Pd), Gold (Au), Titanium (Ti), Platinum (Pt), Platinum-Iridium (Pt—Ir), metallic alloys comprising a plurality of these metals, and/or the like. It will be appreciated, however, that other biocompatible metals or non-metallic electrically conductive materials may be used. The biocompatible metallization may thus utilize seed deposition and plating, thin laminated foils for conductors, printed conductors, doped polymer traces, physical vapor deposition, chemical vapor deposition, and/or the like.

Once the interconnect 138 is fabricated on the insulator 140, the insulating layer 134 is applied to the insulator 140 over the interconnect 138. In one implementation, the insulating layer 134 is applied with intimate contact between the inner surface of the insulator 140 and an inner surface of the insulating layer 134 outside the trace pattern of the interconnect 138. Stated differently, after application, there is intimate contact between the inner surface of the insulator 140 and the inner surface of the insulating layer 134 where there are no traces, thereby encapsulating the interconnect 138 between the insulator 140 and the insulating layer 134. The insulating layer 134 may be made from an insulating material, including, without limitation, polyimide, organic thermoplastic polymer (e.g., PEEK), LCP, glass, ceramic, inorganic material, non-conductive oxide, thermoset polymer, and/or other flexible or rigid insulating materials. The insulating layer 134 may be applied through extrusion, coating, casting, deposition, lamination, printing, and/or the like.

In one implementation, once the insulating layer 134 is applied, the interconnect 138 is encapsulated between the insulating layer 134 and the insulator 140. In another implementation, the insulating layer 134 and the interconnect 138 are part of a multiple-layer series of alternating insulating and conducting layers. Stated differently, the thin film feedthrough 100 may include conductive traces in a plurality of layers separated by insulating layers. The thin film feedthrough 100 may thus include multiple layer traces and outer layer connections to support a higher number of electrical pathways for channels while minimizing the footprint of implantable electronic system 70, among other advantages.

The external electrode contacts 130 and the internal electrode contacts 132 may be formed on an outer surface of the insulator 140 and/or the insulating layer 134. In one implementation, the external electrode contacts 130 and the internal electrode contacts 132 are in electrical communication with the interconnect 138 to form the thin film feedthrough 100. Electrical communication between the interconnect 138 and the external electrode contacts 130 and the internal electrode contacts 132 may be established in a variety of manners. For example, in one implementation, one or more vias are formed in the outer surface of the insulator 140 and/or the insulating layer(s) 134 and filled with conductive material to establish the electrical communication between pads of the interconnect 138 and the external electrode contacts 130 and the internal electrode contacts 132 at the header connection end traces and the internal connection end traces, respectively.

Figure 6A:
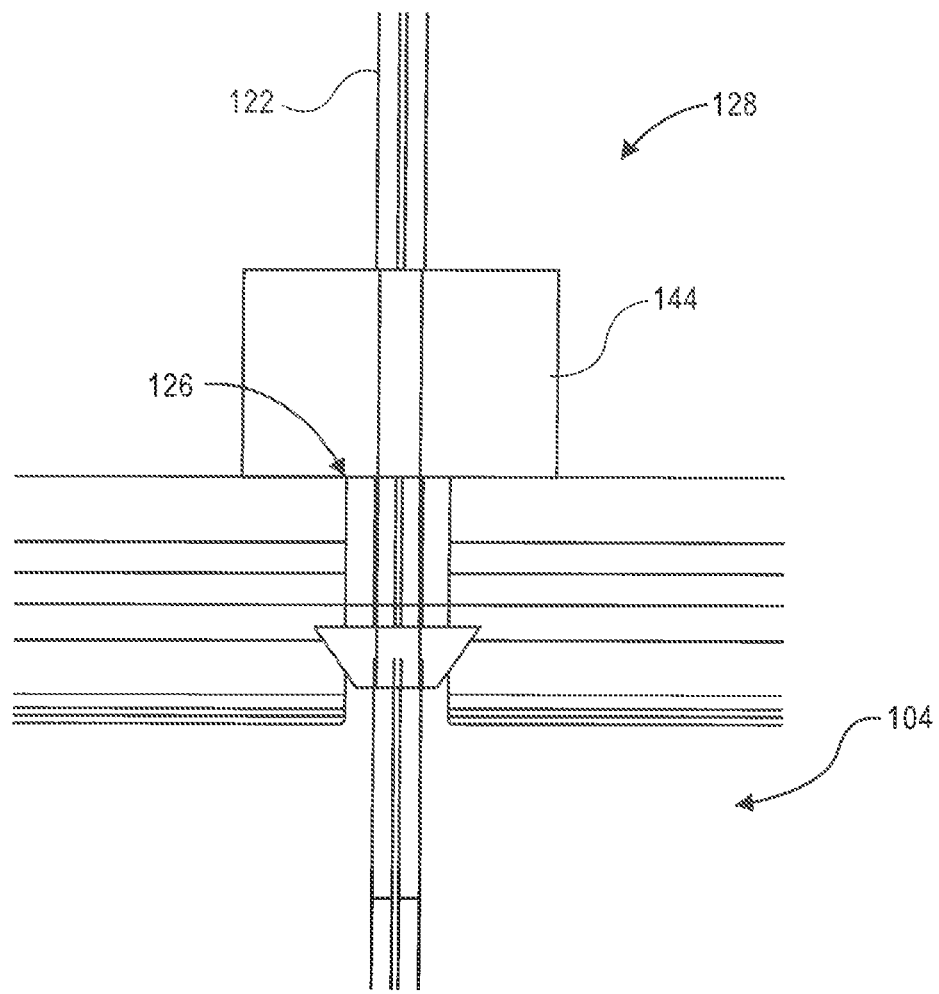
FIG. 6A is a detailed view of an example hermetic junction for the thin film feedthrough prior to sealing.
Figure 6B:
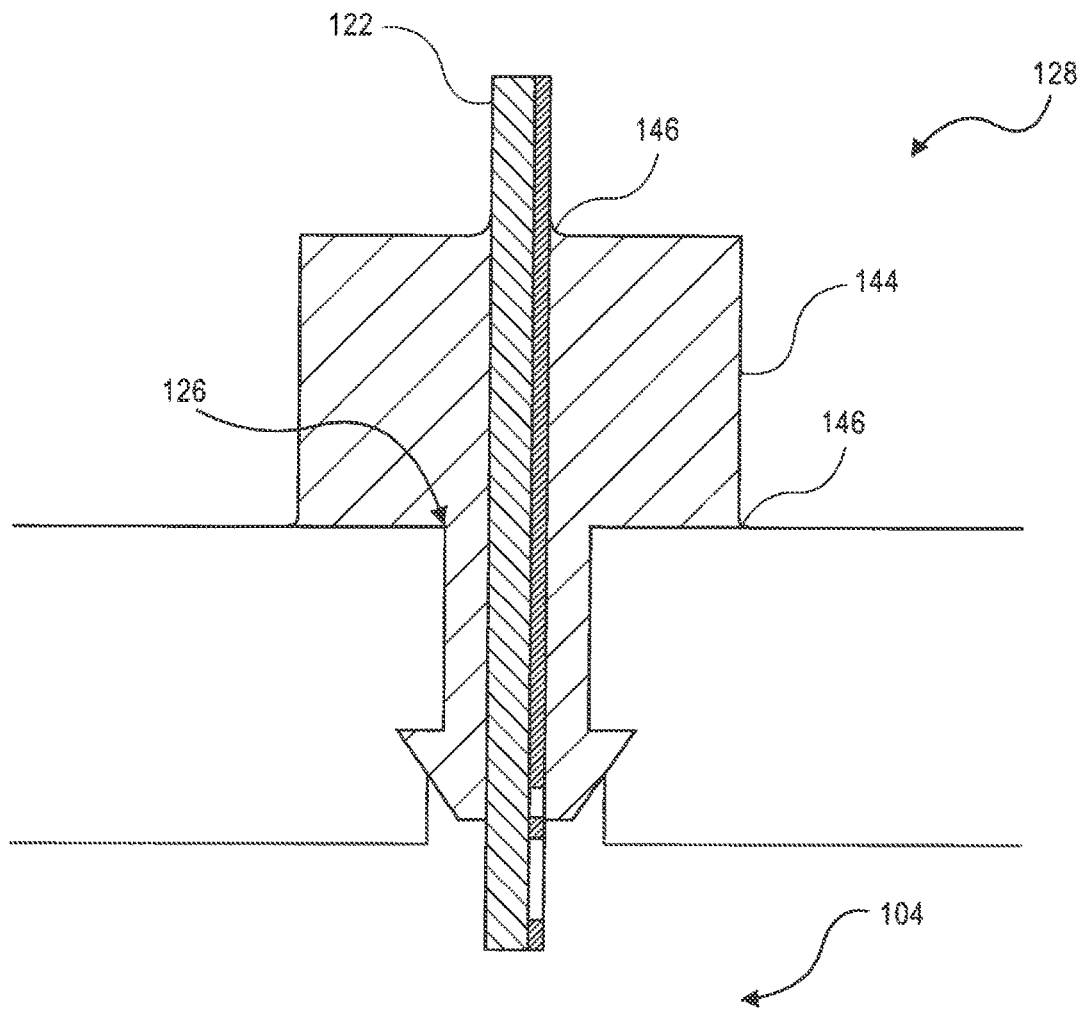
FIG. 6B shows the hermetic junction of FIG. 6A following sealing.

As can be understood from FIG. 6A, in one implementation, the feedthrough body 122 of the thin film feedthrough 100 extends through the feedthrough port 126 of the housing 102 into the hermetic environment 104. To isolate and seal the hermetic environment 104 from the outside, the thin film feedthrough 100 includes the hermetic junction 128 deployed within the feedthrough port 126 to hermetically seal the feedthrough port 126, isolating the hermetic environment 104 from surrounding patient tissue and fluid. The hermetic junction 128 may include a flange 144 sealed at one or more interfaces through hermetic sealing 146, as shown in FIG. 6B. The hermetic sealing 146 may include a first hermetic sealing interface between the flange 144 and the feedthrough body 122 and/or a second hermetic sealing interface between the flange 144 and/or an external surface of the housing 102. The flange 144 may be made from LCP, metal, glass, and/or otherwise through the application of a sealant, such as an epoxy, annealed glass, or polymer, which forms a contiguous bond and isolates the hermetic environment 104. The thin film feedthrough 100 directly transmits discrete electronic signals between the internal electronic components disposed within the hermetic environment 104 and external contacts disposed outside the hermetic environment 104.

As can be understood from FIGS. 6A-6B, the presently disclosed technology incorporates the hermetic junction 128 around the thin film feedthrough 100, providing a barrier between the external and internal areas (i.e., outside and inside the hermetic environment 104) on an IED. The thin film feedthrough 100 enables a much smaller sized feedthrough port 126 to be utilized than the conventional feedthrough technologies to allow the thin film feedthrough 100 to span the internal and external areas. The smaller feedthrough port 126 enables the location of the feedthrough port 126 to be optimized for assembly and the forming of the hermetic junction 128.

There are many options to form the hermetic junction 128, for example those illustrated in FIGS. 6A-6S, which entail creating a hermetic seal between the dielectric substrate/surface on the thin film feedthrough 100 and the surface around the feedthrough port 126 in the housing 102. In one implementation, the hermetic junction 128 is created by applying a bead of hermetic adhesive around the intersection of the feedthrough body 122 and the feedthrough port 126. The selection of the hermetic adhesive may depend on the ability to bond to the materials utilized in the feedthrough body 122 and the surface of the housing 102. The surfaces of the feedthrough body 122 and the housing 102 may be pretreated using processes, such as solvent cleaning, plasma, corona, flame, etching, roughening, and/or the like to ensure the desired seal of the hermetic junction 128 is achieved. A hermetic epoxy may be used to provide the hermetic junction 128.

In another implementation, a pre-molded hermetic flange 144 or gasket is designed to fit around the feedthrough body 122 and fill/engage with the feedthrough port 126. The flange 144 can be pre-molded directly onto the feedthrough body 122 in a corresponding location creating the hermetic junction 128 with the thin film feedthrough 100. The flange 144 and the thin film feedthrough 100 can then be inserted into the housing 102 until they are properly aligned with the feedthrough port 126.

Once the flange 144 is in place there are several options to provide a hermetic seal to the housing 102. In one implementation, the flange 144 may be compressed to create the hermetic sealing 146 either by forcing the flange 144 into the feedthrough port 126 or by compressing the feedthrough port 126 around the flange 144. Another implementation utilizes heat to reflow the material of flange 144 around the feedthrough port 126 to form the hermetic sealing 146 at the hermetic junction 128. Here, the material of the flange 144 does not have a melting temperature higher than the material of the feedthrough body 122. In still another implementation, a solvent or glue is utilized to bond the flange 144 around the feedthrough port 126 to create the hermetic junction 128.

Turning to FIGS. 6C-6E, an example of the flange 144 for forming the hermetic junction 128 is provided. In one implementation, the flange 144 comprises an LCP body having a first set of body surfaces 150 connected to each other by a second set of body surfaces 152. The first set of body surfaces 150 may be disposed perpendicularly to the second set of body surfaces 152, forming a rectangular shaped LCP body. A proximal body surface 148 extends between the first set of body surfaces 150 and the second set of body surfaces 152.

In one implementation, the flange 144 includes a neck 154 extending between the LCP body and a retaining lip. The neck 154 may be rectangular in shape and made from LCP. However, other shapes and compositions are contemplated. In one implementation, the retaining lip is made from LCP and includes a first set of retaining surfaces 158 connected to each other by a second set of retaining surfaces 160. The first set of retaining surfaces 158 and the second set of retaining surfaces 160 each extend at an inward angle, such that the retaining lip tapers in thickness from a proximal retaining surface 156 to a distal retaining surface 164. The flange 144 includes a slot 162 extending from the proximal body surface 148 to distal retaining surface 164.

As shown in FIGS. 6A-6B, in one implementation, the slot 162 is adapted to permit the feedthrough body 122 to extend therethrough from external areas into the hermetic environment 104. More particularly, in one implementation, the flange 144 is positioned with the LCP body against an external surface of the housing 102 with the neck 154 extending into the feedthrough port 126. The proximal retaining surface 156 of the retaining lip may hold the flange 144 in position within the feedthrough port 126.

To form the hermetic junction 128 with the flange 144, the LCP material of the flange 144 may be welded to the housing 102 and/or the feedthrough body 122, creating the hermetic sealing 146 shown in FIGS. 6B, 6F, and 6G. In one implementation, the flange 144 is overmolded onto the feedthrough body 122 with the hermetic sealing 146, and the feedthrough body 122 is fed through the feedthrough port 126 into the interior of the housing 102 until the flange 144 is moved into the feedthrough port 126. The flange 144 may then be heated to bond the LCP body of the flange 144 to the housing 102 to create the hermetic sealing 146 and form the hermetic junction 142 between the exterior and hermetic environment 104.

In another implementation, the feedthrough body 122 extends through the slot 162, such that the flange 144 slides freely along the feedthrough body 122. The flange 144 may be one integral piece or a plurality of pieces each slidable along the feedthrough body 122. The flange 144 is slid into the feedthrough port 126 and the feedthrough body 122 oriented relative to the flange 144 in a desired position aligning the internal electrode contact 132 according an arrangement of the internal components within the hermetic environment 104. Once the flange 144 is positioned in the feedthrough port 126 and the feedthrough body 122 oriented accordingly, heat may be applied to reflow the LCP material of the flange to create the hermetic sealing 146 and form the hermetic junction 128. The hermetic sealing 146 may be created by reflowing the proximal body surface 148 onto the feedthrough body 122 and/or by reflowing the first and second set of body surfaces 150 and 152 onto the housing 102.

In each of these implementations, the LCP material may be reflowed to create the hermetic sealing 146 through a variety of heating processes. For example, a laser may be used to apply localized heat to the LCP body of the flange 144 until the LCP material reflows and forms the hermetic sealing 146. The LCP material has a lower melting point than a melting point of the housing 102 and the feedthrough body 122. The heat source may be a two micron laser or similar localized heat source that would melt the LCP of the flange 144 but not the material of the feedthrough body 122 or the housing 102. The LCP material of the flange 144 would therefore be reflowed onto the feedthrough body 122 and/or the housing 102 to create the hermetic sealing 146 without damaging the feedthrough body 122 or the housing 102. Similarly, localized infrared heat may be applied to the LCP body of the flange 144 to reflow the LCP material. As another example, the flange 144 may be ultrasonically welded to the housing 102 and/or the feedthrough body 122, creating the hermetic sealing 146. It will be appreciated that other heating and/or welding processes may be used to create the hermetic sealing 146 to form the hermetic junction 128.

In addition or alternative to the boding of the flange 144 through heating, the hermetic sealing 146 may be created through various mechanical processes, such as crimping. In one implementation, a band is positioned around the flange 144, compressing the flange 144 around the feedthrough body 122 within the slot 162. With the flange 144 crimped against the feedthrough body 122, the band and/or the LCP material of the flange 144 are welded to the housing 102. The band may be made from a metal, such as Titanium, or other materials described herein. In one implementation, the metal of the band melts and/or the LCP material of the flange 144 reflows to create the hermetic sealing 146 interface between the housing 102 and the flange 144.

Turning to FIGS. 6H-6M, another example of the flange 144 for forming the hermetic junction 128 is provided. In one implementation, the flange 144 comprises a ring having a ring body 170 extending between a proximal ring surface 166 and a distal ring surface 168. The ring body 170 may be made from a variety of materials, including but not limited to, metal, such as Titanium, glass, and/or the like. The ring body 170 includes a slot 172 extending from the proximal ring surface 166 to distal ring surface 168. The slot 172 is adapted to permit the feedthrough body 122 to extend therethrough from external areas into the hermetic environment 104.

As illustrated in FIGS. 6K-6M, the ring body 170 may be heated and/or crimped to form the hermetic sealing 146 at the interface with the housing 102 and/or the feedthrough body 122. In one implementation, the feedthrough body 122 extends through the feedthrough port 126 and fits within the slot 172 of the ring body 170 snugly, with the distal ring surface 168 positioned against an external surface of the housing 102. A heating process, such as those described above, may be used to melt the ring body 170 onto the external surface of the housing 102, thereby creating the hermetic sealing 146 of the hermetic junction 148. This heating process may further cause the LCP or similar material of the feedthrough body 122 to reflow to bond the ring body 170 of the flange 144 to the feedthrough body 122 as well.

In another implementation, the ring body 170 is integral with the housing 102, such that the feedthrough port 126 includes the flange 144 as a puncture port into the housing 102. Here, the ring body 170 may be similarly heated to reflow the material of the feedthrough body 122 to bond the feedthrough body 122 to the housing 102 to create the hermetic sealing 126 of the hermetic junction 128.

As can be understood from FIGS. 6N-6P, an example of the hermetic sealing 146 includes a glass bead 174. In one implementation, the glass bead 174 is applied around the feedthrough port 126 with the feedthrough body 122 extending therethrough in a slot 176. Heat is applied using a heat source, such as a laser, heat gun, oven, and/or the like to anneal the glass bead 174, thereby creating the hermetic sealing 146 to form the hermetic junction 128. It will be appreciated that other heating processes, such as those described herein, may alternatively or additionally be used.

FIGS. 6Q-6S illustrate another example of the hermetic sealing 146 in the form of a hermetic epoxy 178. In one implementation, the feedthrough body 122 is inserted through the feedthrough port 126 and oriented as desired. A bead of epoxy, LCP with a solvent, or similar adhesive with a low leak rate is applied around the interface of the feedthrough body 122 and the feedthrough port 126, and the epoxy is cured to form the hermetic sealing 146 in the form of the hermetic epoxy 178, such that the feedthrough body 122 extends through a slot 180 in the hermetic epoxy 178. The epoxy may be cured into the hermetic epoxy 178 through a variety of curing processes, such as letting the epoxy cure on its own or accelerated using localized heat. The localized heat may be applied using ultraviolet light, an oven, a laser, a heat gun, and/or the like. Additionally or alternatively, the localized heat may be applied using any of the heating processes described herein.

When the thin film feedthrough 100 is fabricated, a bond is formed between substrate layers, which can be achieved in several methods, including, without limitation, the addition of an adhesive between the layers, thermal bonding, coating, and/or the like. The use of an adhesive may be an option for thin film feedthrough 100 if it is to be fully encapsulated within the external surfaces of the IED 90 however the adhesive may impact the moisture absorption rate of the composite and thus reduce the level of hermiticity the thin film feedthrough 100 can provide. If any exposure to bodily fluids is expected, the use of adhesive may also pose a more complex biocompatibility challenge than directly bonding like materials together. The LCP material offers the option to slightly vary the glass transition temperature (Tg) of the raw material, thereby enabling thermal bonding of two LCP layers directly together without distorting the electrical pathways on the substrate layer with the higher Tg. Forming thin film feedthroughs 100 from LCP can be achieved in several methods including but limited to solvent casting and extrusion. In one implementation, an extrusion process utilizes a counter rotating die in the extruder head to provide uniform dimensional and physical stability to the thin film feedthrough 100.

Figure 7A:
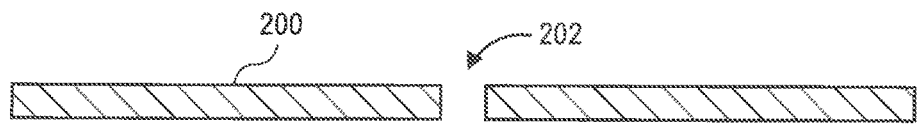
FIGS. 7A-7E show a plated through hole integration process for forming a thin film feedthrough.
Figure 7B:
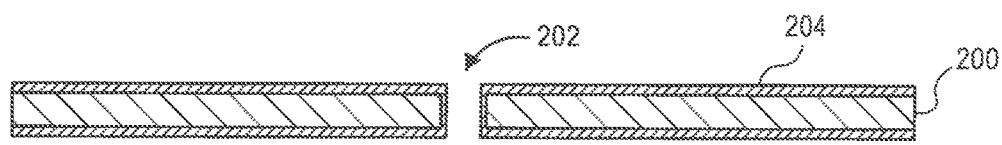
Figure 7C:
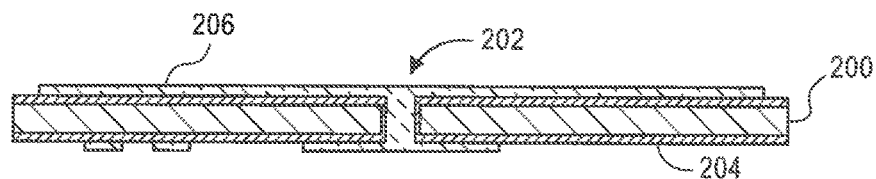
Figure 7D:
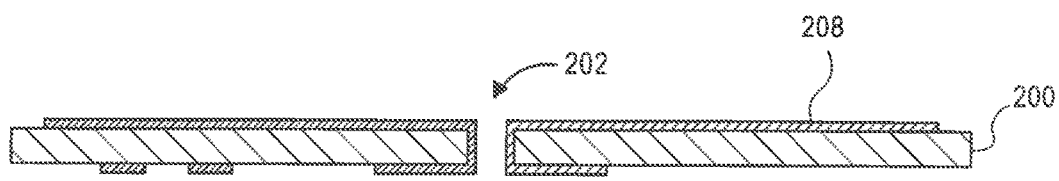
Figure 7E:
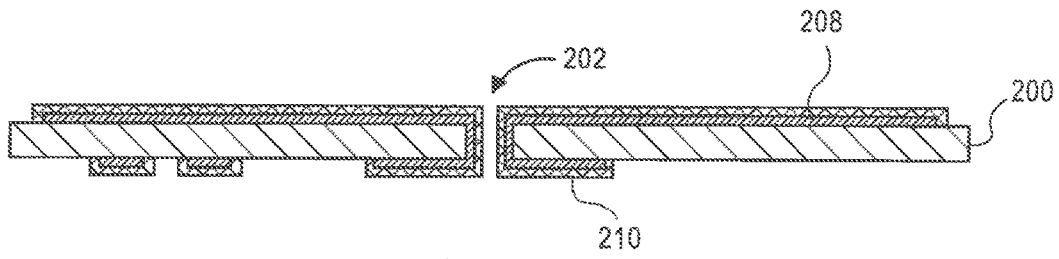

For a detailed description of example manufacturing processes associated with the thin film feedthrough 100, reference is made to FIGS. 7A-12. Turning first to FIGS. 7A-7E, a detailed description of an example plated through hole integration process is provided. In one implementation, a substrate 200 is formed. One or more vias 202 are formed in the substrate 200, as shown in FIG. 7A. In one implementation, the vias 202 are laser drilled. As shown in FIG. 7B, a conductive seed layer 204 is deposited on one or more surfaces of the substrate 200. The conductive seed layer 204 may comprise one or more layers of biocompatible metal. Turning to FIGS. 7C-7D, a trace pattern 208 is defined in the conductive seed layer 204. In one implementation, resist 206 is deposited to pattern the conductive seed layer 204. The conductive seed layer 204 is etched and the resist 206 is removed, thereby forming the trace pattern 208. As can be understood from FIG. 7E, an electroplate 210 is deposited on the trace pattern 208.

Figure 8A:
FIGS. 8A-8G depict a sequential metal integration process for forming a thin film feedthrough.
Figure 8B:
Figure 8C:
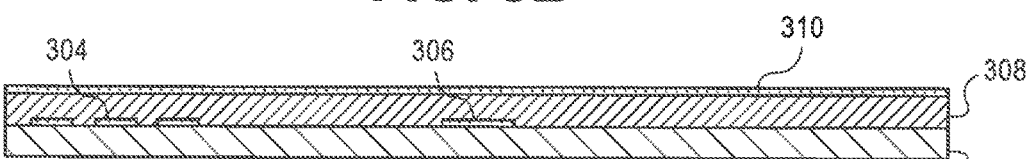
Figure 8D:
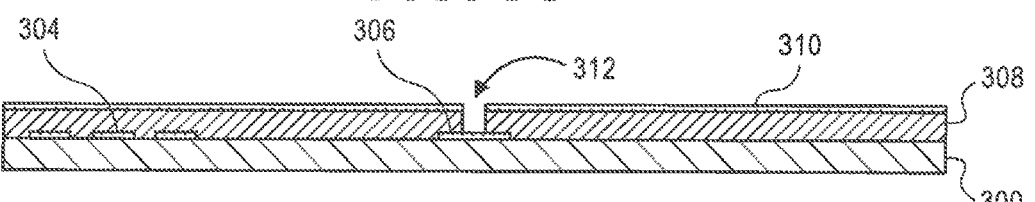
Figure 8E:
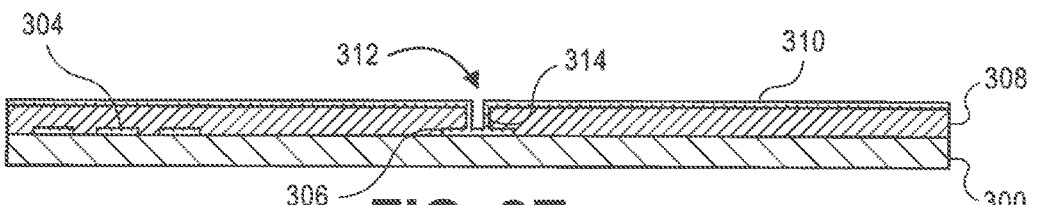
Figure 8F:
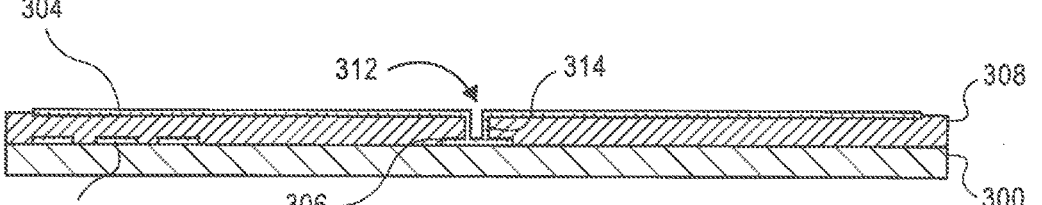
Figure 8G:
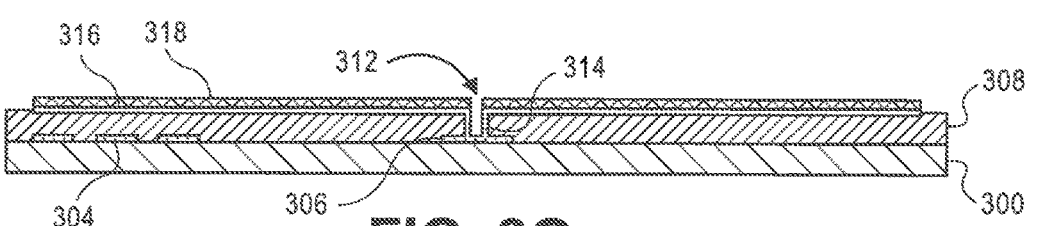

Referring next to FIGS. 8A-8G, an example sequential metal integration process is illustrated. Referring first to FIG. 8A, in one implementation, a first substrate 300 is formed, and a first conductive layer 302 is deposited on one or more surfaces of the substrate 300. The first conductive layer 302 may comprise one or more layers of biocompatible metal. As shown in FIG. 8B, the first conductive layer 302 is patterned and wet etched to form a trace patter with one or more conductive interconnects 304 and 306. In the alterative, a conductive seed layer, through mask plate, and seed etch may be used. Turning to FIG. 8C, a second substrate 308 is laminated to the first substrate 300 over the conductive interconnects 304 and 306, and a second conductive layer 310 is deposited on at least one of an outer surface of the first substrate 300 or the second substrate 308. FIG. 8D shows at least one via 312 formed in the first substrate 300 or the second substrate 308 depending on the deposition of the second conductive layer 310. In one implementation, the via 312 is laser drilled through the second conductive layer 310 and the second substrate 308 to expose the conductive interconnect 306 of the trace pattern. FIG. 8E illustrates the via 312 plated with a thick conductive via fill 314, which may be a thick noble metal, such as gold, to electrically connect the second conductive layer 310 to the trace pattern. Turning to FIGS. 8F-8G, the second conductive layer 310 is patterned and etched to form internal or external electrode contacts 316, with an electroplate 318 deposited thereon.

It will be appreciated that in other implementations, the integration process may include drilling the one or more vias 312 in the first substrate 300 and/or the second substrate 308 and depositing the second conductive layer 310 thereon. The second conductive layer 310 is patterned to form the electrode contacts 316, and the electroplate 318 is deposited to plate the electrode contacts 316. The via(s) are plated with the thick conductive via fill 314. Other implementations of the integration process are further contemplated.

Figure 9A:
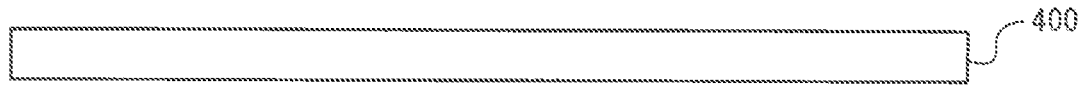
FIGS. 9A-9I illustrate a glass feedthrough process for forming a thin film feedthrough.
Figure 9B:
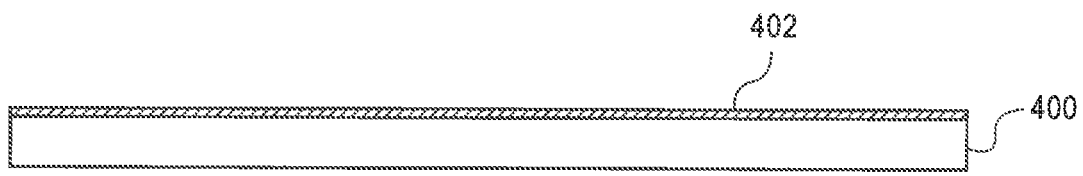
Figure 9C:
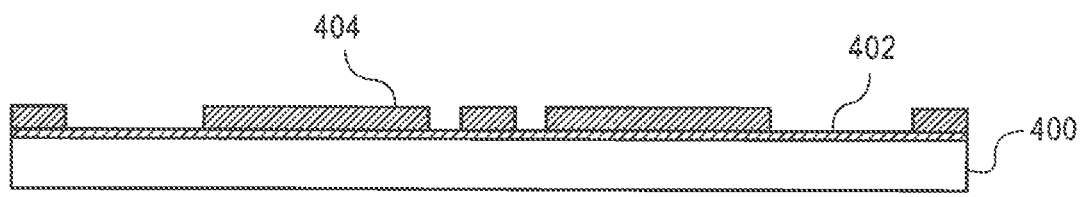
Figure 9D:
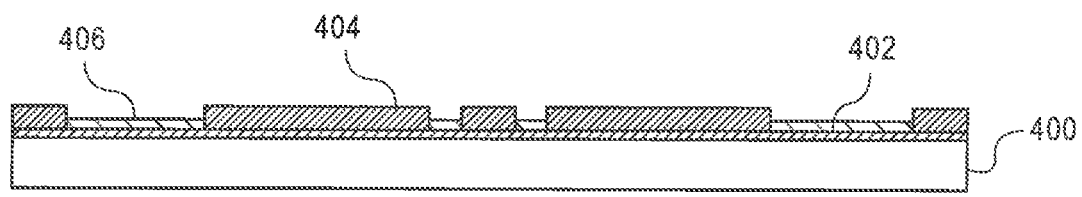
Figure 9E:
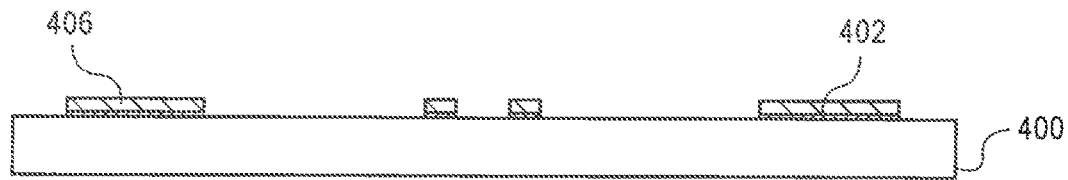
Figure 9F:
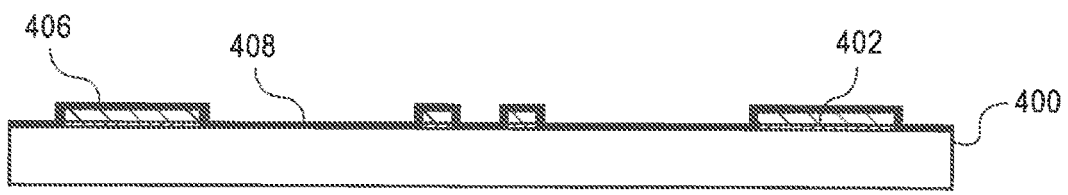
Figure 9G:
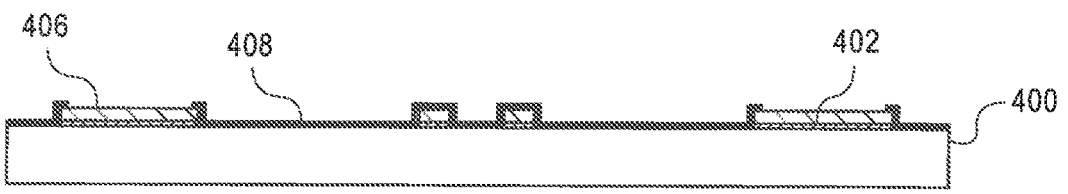
Figure 9H:
Figure 9I:
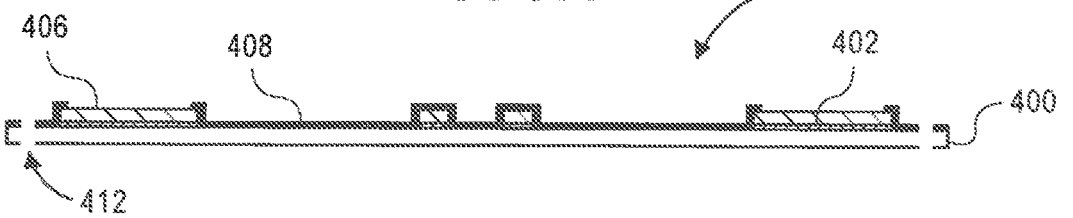

Turning next to FIGS. 9A-9I, an example glass feedthrough process is illustrated. In one implementation, a glass substrate 400 is provided, as shown in FIG. 9A. Turning to FIG. 9B, an electroplating seed layer 402 is deposited on at least one surface of the glass substrate 400. The electroplating seed layer 402 is patterned to form a trace pattern 404 with one or more conductive interconnects and/or pads, as shown in FIG. 9C. The electroplating seed layer 402 may be patterned using photolithography, for example, through photoresist and processing parameters, including but not limited to, coating, exposing, and developing. Turning to FIG. 9D, the trace pattern 404 is plated with a conductive material, such as a noble metal, to form a primary conducting layer 406. FIG. 9E illustrates the removal of patterned resist with solvent strip, plasma strip, and/or other resist removal processes, and FIG. 9F shows a thin passivation layer 408 deposited over the primary conducting layer 406. As shown in FIG. 9G, the passivation layer 408 is patterned and etched for pad openings to the primary conducting layer 406, for example, using photolithography. Turning to FIGS. 9H-9I, the glass substrate 400 is thinned to generate a thin film feedthrough 410, and laser dicing is performed to singulate individual feedthrough devices 412.

Figure 10:
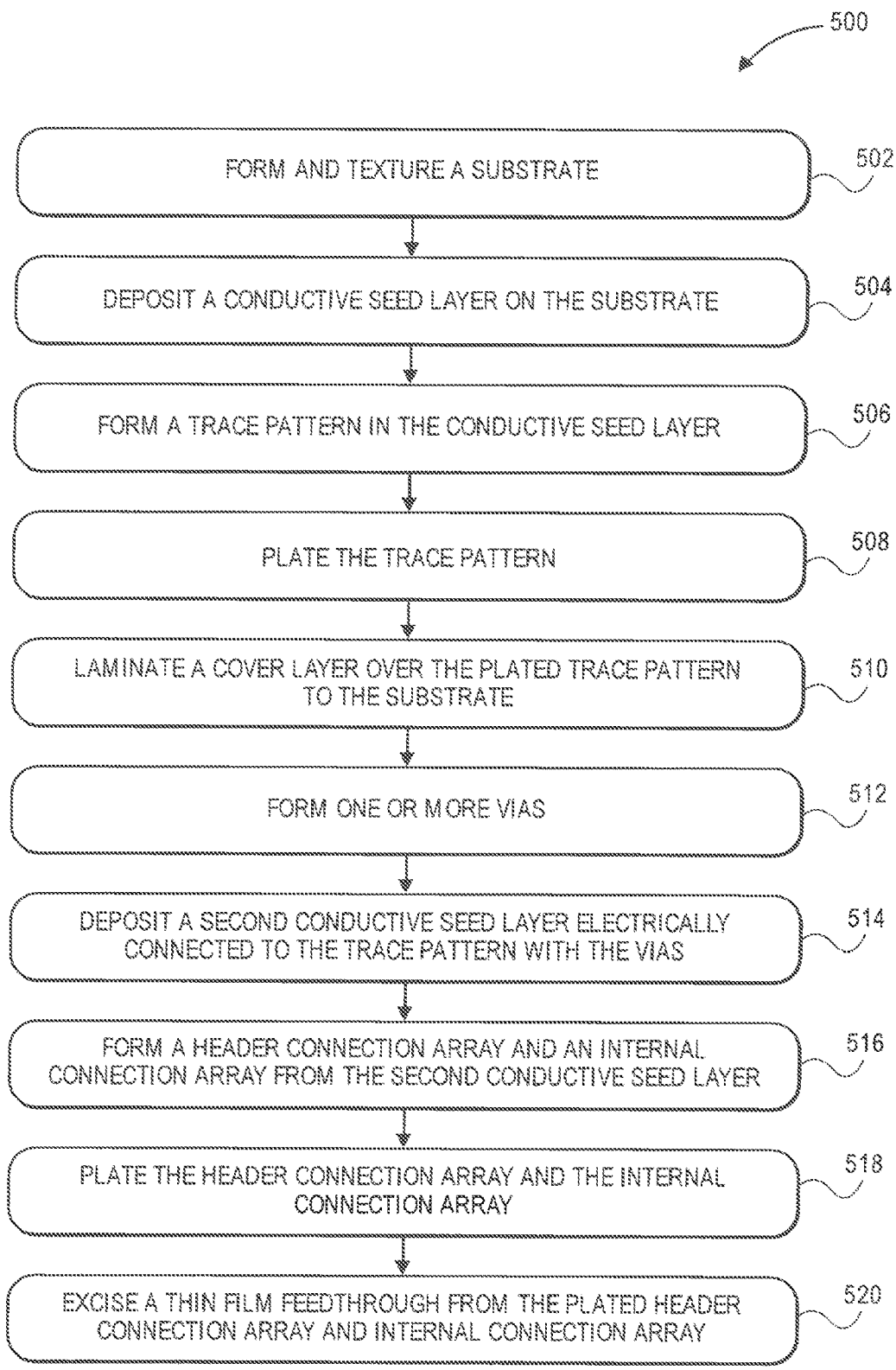
FIG. 10 illustrates example operations for forming a thin film feedthrough from a two-dimensional substrate.

Referring next to FIG. 10, example operations 500 for forming a thin film feedthrough from a two-dimensional substrate are illustrated. In one implementation, an operation 502 forms and textures a substrate. More particularly, in one implementation, the operation 502 provides raw material which may be, for example, an LCP substrate or a substrate with an LCP overlay. The thickness of the layer of LCP may be approximately 10-100 microns. In one example, the LCP has a thickness of approximately 25-50 microns. The operation 502 then textures the raw material for bonding. The raw material may be textured, for example, using O2 plasma texture, Ar texture, a wet texture, and/or mechanical abrasion.

In one implementation, an operation 504 deposits a conductive seed layer on the substrate. The conductive seed layer may be deposited following an adhesion layer comprising Cr, Ti, Pd, and/or the like. The conductive seed layer may comprise one or more layers of biocompatible metals, such as noble metals. In one implementation, the operation 504 vacuum deposits two sequential layers of Ti/Au with approximately 500-5000 Angstroms of Au over approximately 100-1000 Angstroms of Ti. An operation 506 forms a trace pattern in the conductive seed layer. In one implementation, the operation 506 deposits resist for patterning and performs a two stage etching of wet and/or dry etching. The trace pattern formed by the operation 506 may include final line and space from approximately 10-100 microns with a number of channels ranging from 1 to 256 or greater depending on a geometry of the thin film feedthrough. An operation 508 plates the trace pattern. In one implementation, approximately 1-15 microns of Au are plated on top of the trace pattern.

In one implementation, an operation 510 laminates a cover layer over the plated trace pattern to the substrate. More particularly, an LCP coverlay is laminated to the trace side (i.e., the side of the substrate onto which the conductive seed layer was deposited in the operation 504). In one implementation, the operation 510 manages the glass transition temperature (Tg) of the cover layer and varies the Tg of the substrate to enable thermal bonding of the cover layer to the substrate without distorting the plated trace pattern.

An operation 512 forms one or vias. In one implementation, the operation 512 laser etches or otherwise forms the vias in the cover layer and/or the substrate. The vias may have a diameter ranging from approximately 50-500 microns. In one implementation, the operation 512 fills the vias with a thick noble metal via fill. For example, the operation 512 may plate Au in the vias.

An operation 516 deposits a second conductive seed layer on the cover layer and/or the substrate. The second conductive seed layer is electrically connected to the trace pattern with the plated vias. An operation 518 forms a header connection array and an internal connection array from the second conductive seed layer(s). An operation 518 plates the header connection array and the internal connection array. In one implementation, the operation 518 builds up the header connection array and the internal connection array by plating Au from approximately 1-15 microns to form thick Au electrode and connection arrays, and the operation 518 plates approximately 0.5 to 5 microns of Pt or Pt—Ir over the thick Au electrode and connection arrays to form plated header connection and internal connection arrays. An operation 520 excises a thin film feedthrough with the plated header connection and internal connection arrays. Stated differently, the operations 502-520 form a full tip-to-tail, fully biocompatible flexible circuit feedthrough with in situ fully formed traces, external contacts (e.g., within a header connection assembly to electrically connect to a terminal end of an implantable lead or disposed at a stimulation end of an implantable lead to deliver electrical stimulation), and internal connection contacts (e.g., to connect to internal electrical components within the hermetic environment). The thin film feedthrough uses a thick noble metal plate up to form traces that may have an extended length or are otherwise sized and shaped for a particular configuration of an IED and/or according to a selected dielectric use. Similarly, the thin film feedthrough uses thick noble metal via fill. The thin film feedthrough includes full contacts adapted for connection with internal electrical components and/or the implantable lead without further mechanical and/or metal components, such as attachments, bonds, welds, and/or the like.

Figure 11:
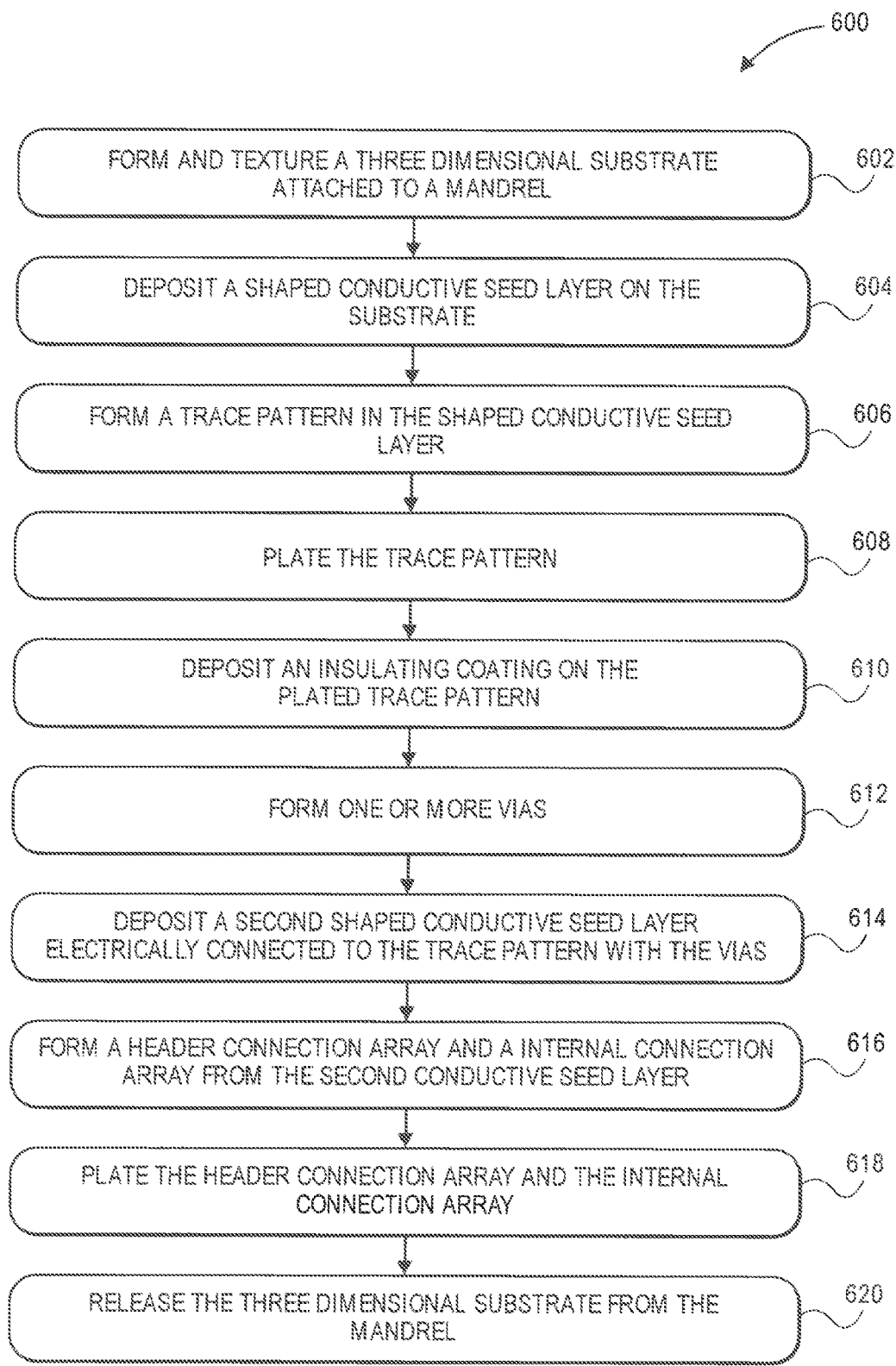
FIG. 11 illustrates example operations for manufacturing a thin film feedthrough from a three-dimensional substrate.

FIG. 11 illustrates example operations 600 for manufacturing a thin film feedthrough from a three-dimensional substrate. In one implementation, an operation 602 forms and texture a three-dimensional substrate attached to a mandrel. More particularly, the operation 602 forms or otherwise provides raw material in the form of a polyimide tube. In one implementation, the polyimide tube has an outer diameter of approximately 30-100 thousandths of an inch and a tube wall of approximately 1-10 thousandths of an inch. The polyimide tube is attached to the mandrel, which may be a Teflon coated stainless steel mandrel. The operation 602 textures the raw material with a plasma and/or a wet process.

An operation 604 deposits a shaped (e.g., cylindrical) conductive seed layer on the substrate. The conductive seed layer may be deposited following an adhesion layer comprising Cr, Ti, Pd. and/or the like. In one implementation, the operation 604 blanket vapor deposits a Ti/Au conductive seed layer around an entirety of the polyimide tube with approximately 500-5000 Angstroms of Au over approximately 100-1000 Angstroms of Ti. An operation 606 forms a trace pattern in the shaped conductive seed layer. In one implementation, the operation 606 uses a three-dimensional inject process to print patterned resist onto the shaped conductive seed layer, and the operation 606 etches the shaped conductive seed layer using a wet/dry etch process or a wet/wet etch process. In another implementation, the operation 606 laser ablates the shaped conductive seed layer into the trace pattern. An operation 608 plates the trace pattern. In one implementation, the operation 608 builds up the traces with a thick Au plate of approximately 1-15 microns.

An operation 610 deposits an insulating coating on the plated trace pattern. In one implementation, the operation 610 dip coats or vapor deposits the insulating coating, which may be a polymer coating, on the plated trace pattern. An operation 612 forms one or more vias. In one implementation, the operation 612 laser ablates or otherwise forms the vias in the insulating coating. In one implementation, the operation 612 fills the vias with a thick noble metal via fill. For example, the operation 612 may plate Au in the vias.

An operation 614 deposits a second shaped conductive seed layer electrically connected to the trace pattern with the vias. In one implementation, the operation 614 blanket vapor deposits the second shaped conductive seed layer of Ti/Au. An operation 616 forms a header connection array and an internal connection array from the second conductive seed layer. In one implementation, the operation 616 patterns the second shaped conductive seed layer using a three-dimensional inkjet process to print patterned resist onto the second shaped conductive seed layer, and the operation 616 etches the second shaped conductive seed layer using a wet/dry or wet/wet etch process. In another implementation, the operation 616 laser ablates the second shaped conductive seed layer into the header connection array and the internal connection array. An operation 618 plates the header connection array and the internal connection array, for example, with a thick noble metal plate, such as an Au plate of approximately 1-15 microns. An operation 620 releases the three dimensional substrate from the mandrel providing a thin film feedthrough that may be connected directly to internal components within a hermetic environment and/or an implantable lead or extend directly from the hermetic environment to a stimulation end configured to stimulate tissue to form an integral thin film feedthrough and lead.

Figure 12:
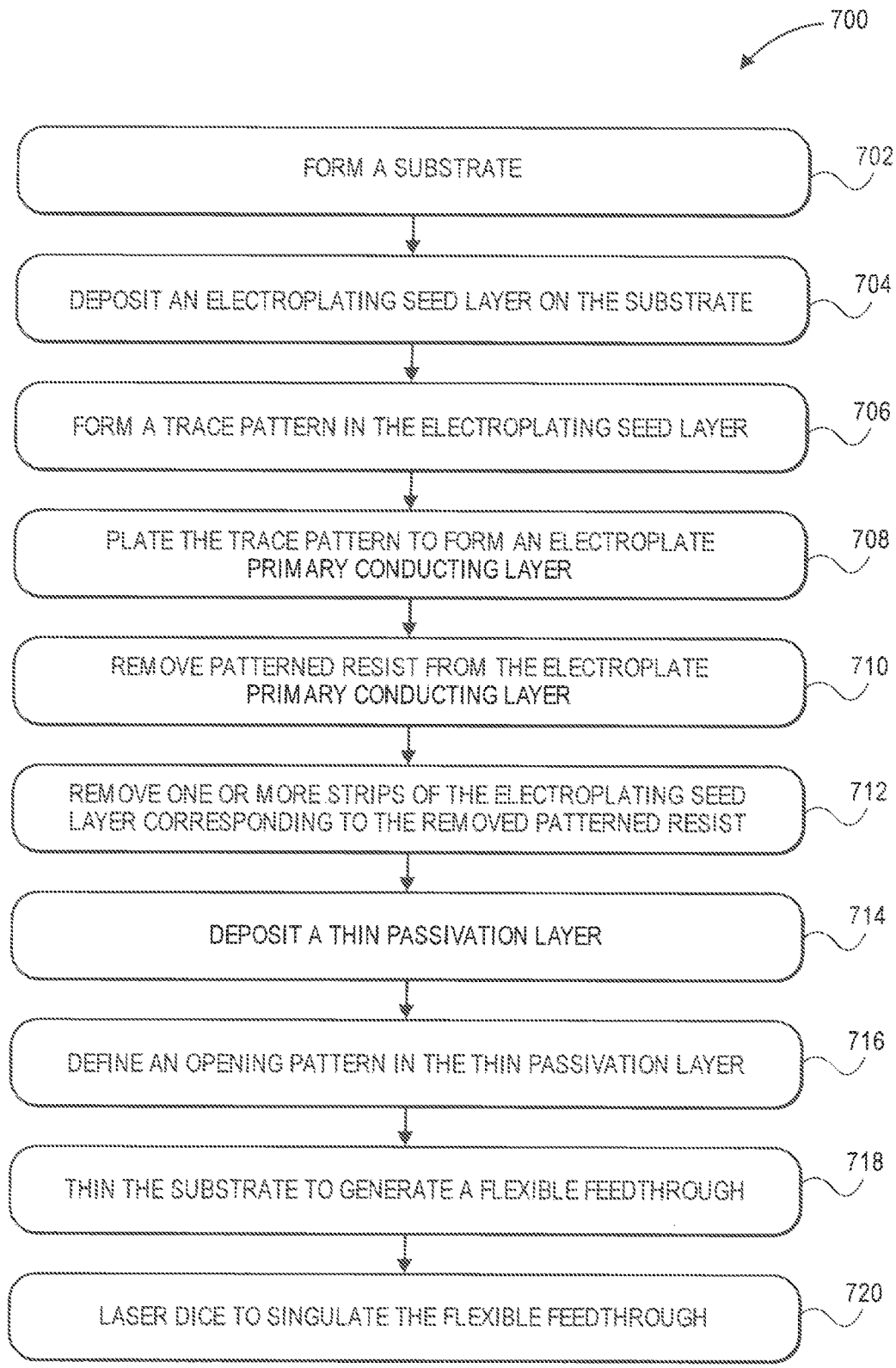
FIG. 12 illustrates example operations for fabricating a thin film feedthrough using a glass feedthrough process.

FIG. 12 illustrates example operations 700 for fabricating a thin film feedthrough using a glass feedthrough process. In one implementation, an operation 702 forms a substrate. The operation 702 may form the substrate from fused silica, single-crystal quartz, glass, ceramics, and/or the like. The substrate may be formed in a semiconductor wafer geometry, which includes a diameter of approximately 150 mm and a semi-standard major flat shape, or a flat panel rectangular geometry.

An operation 704 deposits an electroplating seed layer on the substrate. In one implementation, the operation 704 deposits the electroplating seed layer using physical vapor deposition (PVD). The electroplating seed layer may be deposited following an adhesion layer. The electroplating seed layer may be made from a conductive material, such as Cu, Au, Pt, and/or other noble metals, while the adhesion layer may comprise Cr, Ti, Pd, and/or the like. In one implementation, the operation 704 deposits the adhesion layer thin, for example with a thickness varying from approximately 25-100 nm, while the electroplating seed layer has a thickness ranging from approximately 500-2000 nm.

In one implementation, an operation 706 forms a trace pattern in the electroplating seed layer. The trace pattern, including interconnects and pads, may be defined using photolithography. Photoresist and processing parameters, such as coating, exposing, and developing, used during the photolithography by the operation 706 may depend on the chemistry and thickness of the electroplating seed layer. The operation 706 may form the trace pattern with any number of independent channels, for example, ranging from four to sixteen or more.

An operation 708 plates the trace pattern to form an electroplate primary conducting layer. In one implementation, the operation 708 builds up the traces with a first thick plate of conductive material, such as Au and/or Cu, having a thickness of approximately 5-25 microns. A thin plate of Pt or other noble metal may be deposited over the first thick plate, for example, to form an electrical connection with a particular internal or external electrical component.

In one implementation, an operation 710 removes patterned resist from the electroplate primary conducting layer. The operation 710 may remove the patterned resist with a solvent strip. A solvent based resist strip may be preceded or followed with oxygen plasma ash or alternate plasma ash to improve the resist removal process of the operation 710. An operation 712 removes one or more strips of the electroplating seed layer corresponding to the removed patterned resist. More particularly, in one implementation, the electroplating seed layer is removed with a wet etch where the photoresist was removed. The wet etch may involve a potassium iodide for the Au followed by dilute HF for the Ti, in one example.

An operation 714 deposits a thin passivation layer, which may be, without limitation, silicon dioxide, silicon nitride, and/or other insulating material. In one implementation, the thin passivation layer is deposited using chemical vapor deposition (CVD), such as plasma enhanced CVD, atmospheric CVD, PVD, and/or the like.

An operation 716 defines an opening pattern with one or more pad openings in the thin passivation layer. The opening pattern may be configured to permit physical connections between various electrical pathways and/or components. The opening pattern may be defined using resist and/or processing parameters, for example, depending on a subsequent etch process. In one implementation, the operation 716 etches the passivation layer over the pads to allow access. For example, the operation 716 may utilize a plasma etch or wet etch chemical process, the parameters of which depending on the electroplating material and geometry of the opening pattern.

In one implementation, an operation 718 thins the substrate to generate a thin film feedthrough. The thinning may be performed through physical means, such as lapping or backgrinding, or chemical means, such as a wet chemical etch. The operation 718 thins the substrate while protecting the electrical pathways of the thin film feedthrough, including the trace pattern and pads. An operation 720 laser dices to singulate individual feedthrough devices, while accommodating incongruent dimensions of the thin film feedthrough (i.e., portions not rectangular or square die).

As described herein, the presently disclosed technology provides a thin film hermetically sealed feedthrough, which reduces the complexity, footprint, and cost of the IED 90. The thin film hermetically sealed feedthrough further enables increased channels having smaller and efficient electrical pathways between internal and external components. Moreover, the presently disclosed technology minimizes an otherwise complex assembly process of an IED 90 and implantable electronic system 70 as a whole, thereby permitting the rapid manufacture of customized configurations for particular applications and/or selected dielectric uses.

Generally, the thin film feedthrough 100 comprises a thin film electronic circuit facilitating the transmission of electronic signals between the hermetic environment 104 within an electronic implantable enclosure of an IED and the external connections/contacts configured to deliver therapy and/or receive signals. The presently disclosed technology enables customizable options to optimize the routing of these signals to achieve a desired function, as well as to simplify the assembly process. The thin film feedthrough 100 provides an additional benefit of shrinking the footprint of the electrical pathways and feedthrough geometry through the housing 102.

The thin film feedthrough 100 enables significantly more complex connections and electrical pathways within a much smaller footprint than conventional feedthroughs currently require. The presently disclosed technology provides an additional benefit of isolating the conductive pathways with dielectric material up to a desired location for creating the hermetic junction 128 with a connector/contact thus minimizing the potential for shorting to other conductive elements and/or the hermetic environment 104.

The hermetic junction 128 between the thin film feedthrough 100 and the hermetic environment 104 can be achieved utilizing a low temperature bond from a semi hermetic adhesive, polymer, glass and/or composite thereof applied between the thin film feedthrough 100 and the hermetic environment 104. The hermetic junction 128 may have a minimum leakage rate of less than 10-8 cc/sec and/or reaching 10-9 cc/sec.

FIGS. 13-20 depict various examples of the thin film feedthrough 100, IPG 90, and/or the implantable electronic system 70. It will be appreciated by those of ordinary skill in the art that, along with the examples shown in FIGS. 2-6 such depictions are exemplary only and not intended to be limiting.

Generally, as described herein, the thin film feedthrough 100 is fabricated out of one or more layers of conductive networks encapsulated within a hermetic dielectric material, including, but not limited to a polymer, glass, or composite. In one example, the hermetic dielectric material is LCP, which has superior properties, such as mechanical, thermal, chemical resistance, dielectric strength, low hygroscopicity, dimensional stability, and gas barrier properties.

In one implementation, the thin film feedthrough 100 includes the header connection assembly 120 with external contacts 130 arranged in a header connection array and the internal connection assemble with internal contacts 132 arranged in an internal connection array. The external contacts 130 are disposed outside the hermetic environment 104, for example, enclosed in the header cover 106, and the internal contacts 132 are disposed within the hermetic environment 104. The feedthrough body 122 passes through the small feedthrough port 126 in a wall of the housing 102.

A design of the thin film feedthrough 100 may be customizable according to the internal circuitry of the internal electronic components within the hermetic environment 104 and the external components, such as the implantable lead 80. The size and location of the feedthrough port 126 in the wall of the housing 102 can be easily adjusted based on a layout of the internal electronics and the external contact locations. The number, size, and layers of conductive traces in the thin film feedthrough 100 may define a size, location, and geometry of the feedthrough port 126.

A desired method of assembling the enclosure may also impact the design of the thin film feedthrough 100. For example, if the feedthrough port 126 is created along an open edge of the housing 102, the geometry of the contacts on either end of the thin film feedthrough 100 are unrestricted and can be designed to match any desired connection geometry. If the feedthrough port 126 is created in a closed section of the housing 102, the feedthrough port 126 and/or the end of the thin film feedthrough 100 may be sized to enable one end of the thin film feedthrough 100 to pass through the feedthrough port 126.

The hermetic junction 128 hermetically seals the feedthrough port 126 to isolate the hermetic environment 104 within the housing 102. The hermetic junction 128 may be disposed between the thin film feedthrough 100 and the feedthrough port 126. In this case, the hermetic junction 128 is formed by applying a bead of adhesive around the interface between the thin film feedthrough 100 and the feedthrough port 126. The adhesive material would be capable of meeting the minimum leak rate for the implantable electronic system 70. The design of this interface, along with the material selection for the adhesive, the housing 102, and the dielectric material in the thin film feedthrough 100 further impact the desired leak rate. Surface preparation of the areas to be bonded by the adhesive will enable a stable and consistent seal at the hermetic junction 128. In other implementations, the hermetic junction 128 may include additional components, such as molded/machined inserts utilized to provide enhanced assembly and bonding properties. The hermetic bond of the hermetic junction 128 between the thin film feedthrough 100 and the housing 102 can be created before or after seam welding the housing 102.

The internal connection junctions between the thin film feedthrough 100 and the internal electrical components within the hermetic environment 104 can utilize standard surface mount or through hole technologies, including, but not limited to, surface mount connectors or direct junctions to pads and/or through holes on the thin film feedthrough 100. The external connection junctions between the thin film feedthrough 100 and the external contacts outside the hermetic environment 104 can also utilize surface mount or through hole technologies, as well as direct bonds between the predefined exposed areas of the conductors in the thin film feedthrough 100 and the contacts. The direct bonds can be created utilizing technologies, such as resistance, ultrasonic and/or laser welding. Alternatively, one or more stiffeners can be added to the thin film feedthrough 100 to create an edge connector that can be inserted into edge connector socket to make the necessary electrical connections within the IED 90.

Figure 13:
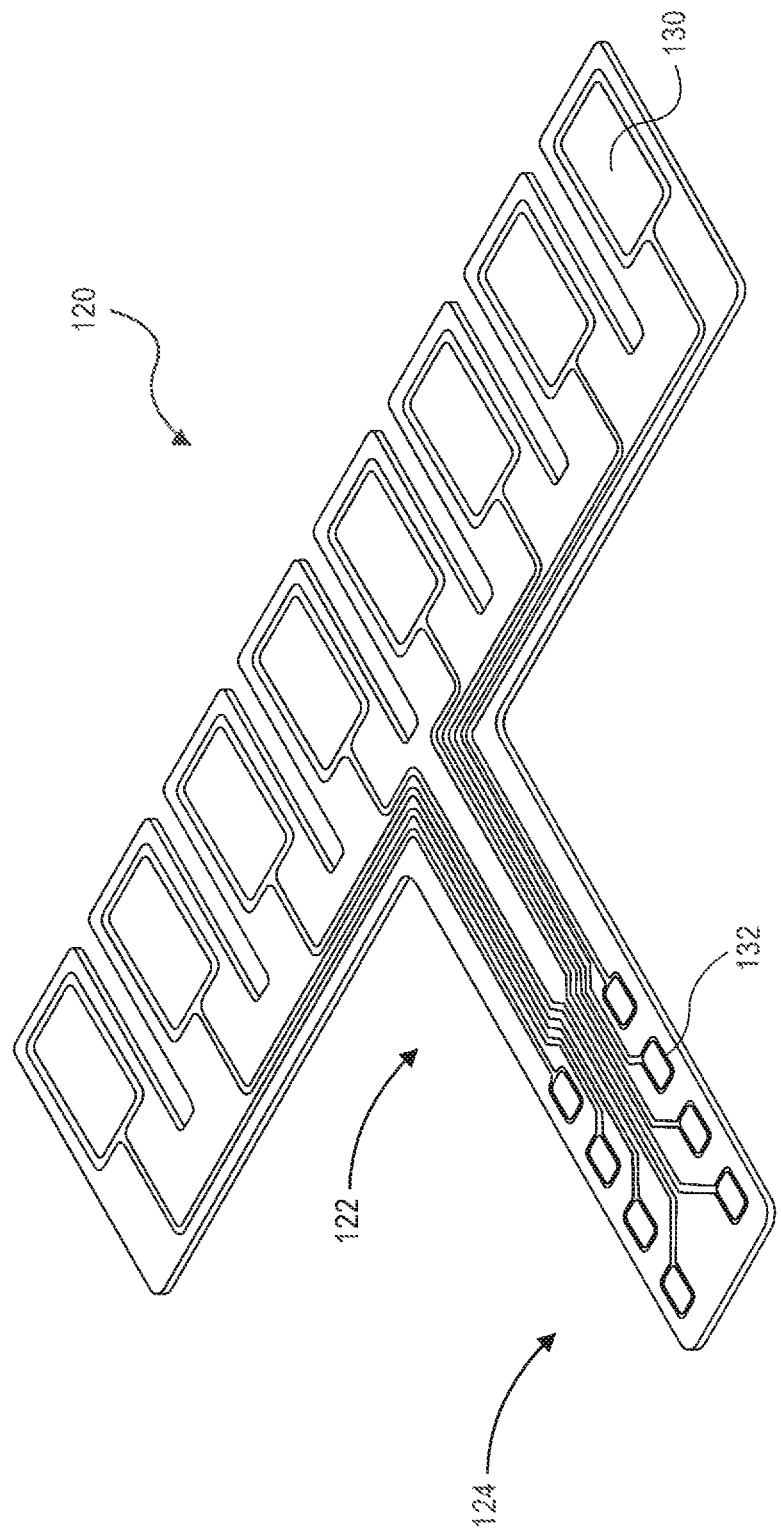
FIG. 13 shows another example thin film feedthrough.
Figure 14:
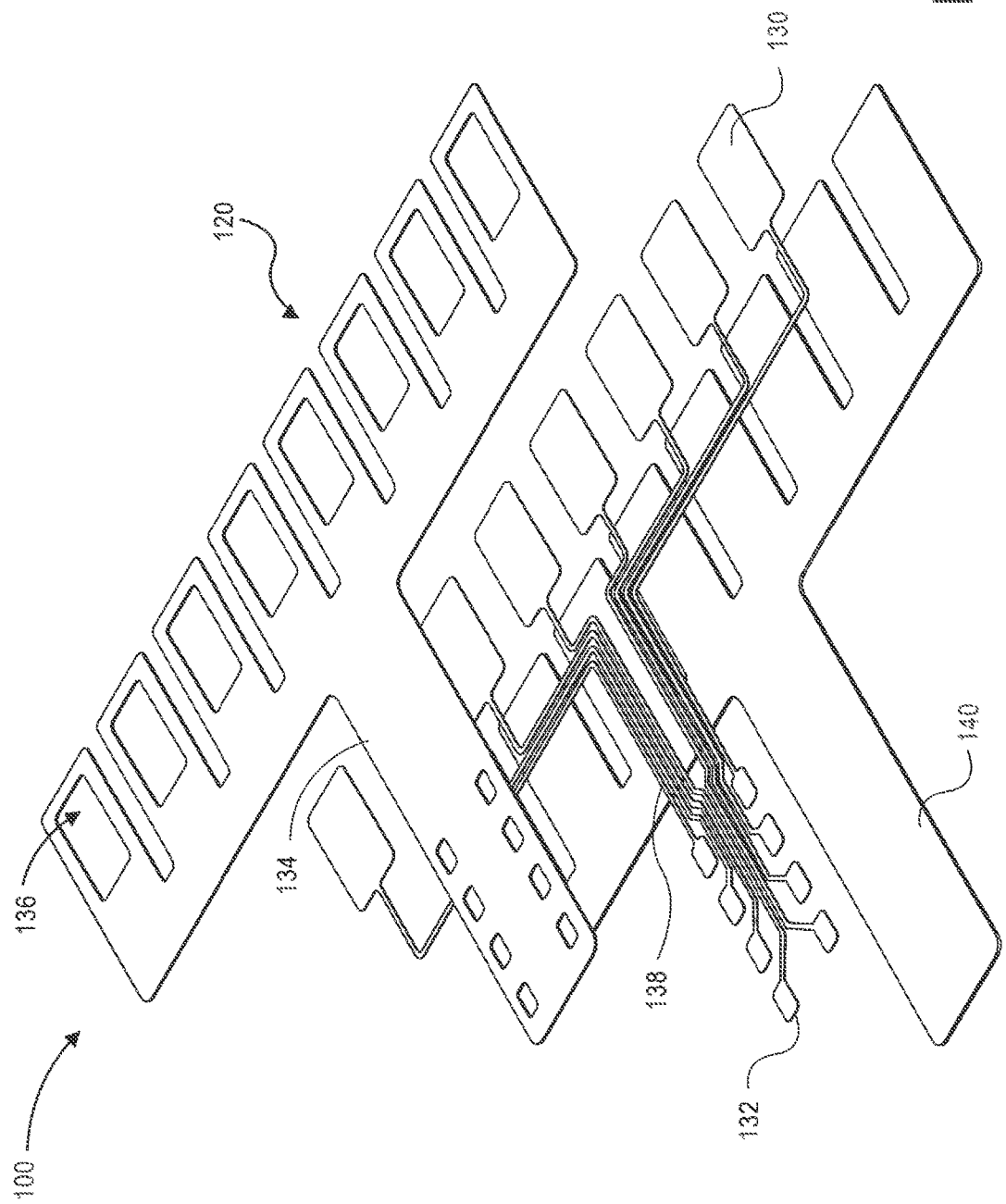
FIG. 14 is an exploded view of the thin film feedthrough of FIG. 13.

Turning to FIGS. 13-20, non-limiting examples of the presently disclosed technology in addition to those shown in FIGS. 2-5 are shown. FIGS. 13-14 show another example of the thin film feedthrough 100. The thin film feedthrough 100 may be fabricated using a plated through hole integration process, a sequential metal integration process, a glass feedthrough process, and/or the like, as described herein.

In one implementation, the thin film feedthrough 100 includes the header connection assembly 120 with a plurality of external electrode contacts 130. Each of the external electrode contacts 130 is in electrical communication with a corresponding internal electrode contact 132 of the internal connection assembly 124 via the feedthrough body 122. The thin film feedthrough 100 may include layers substantially similar to those described with respect to the implementation shown in FIGS. 4-5, including the passivation layer 134 disposed over the interconnection 138 on the substrate 140.

The interconnection 138 includes a trace pattern with the internal connections 132 and the external connections 130. The pad openings 136 are defined in the passivation layer 134 permitting electronic contact with the connections 130 and/or 132.

Figure 15:
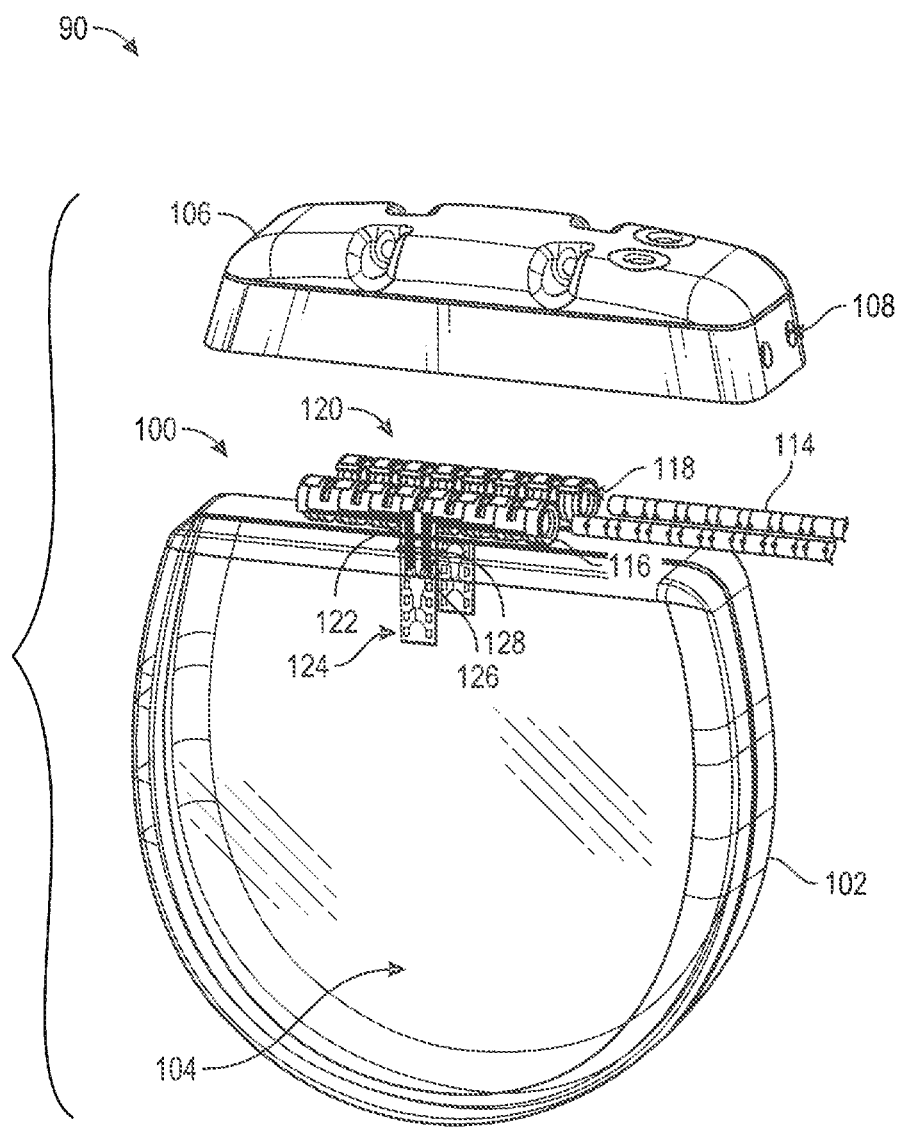
FIG. 15 is an example IED incorporating a set of LCP thin film feedthroughs. The housing of the IED is shown transparent and the header cover is disconnected from the housing for clarity. A hermetic junction of the LCP thin film feedthroughs comprises a LCP flange.
Figure 16:
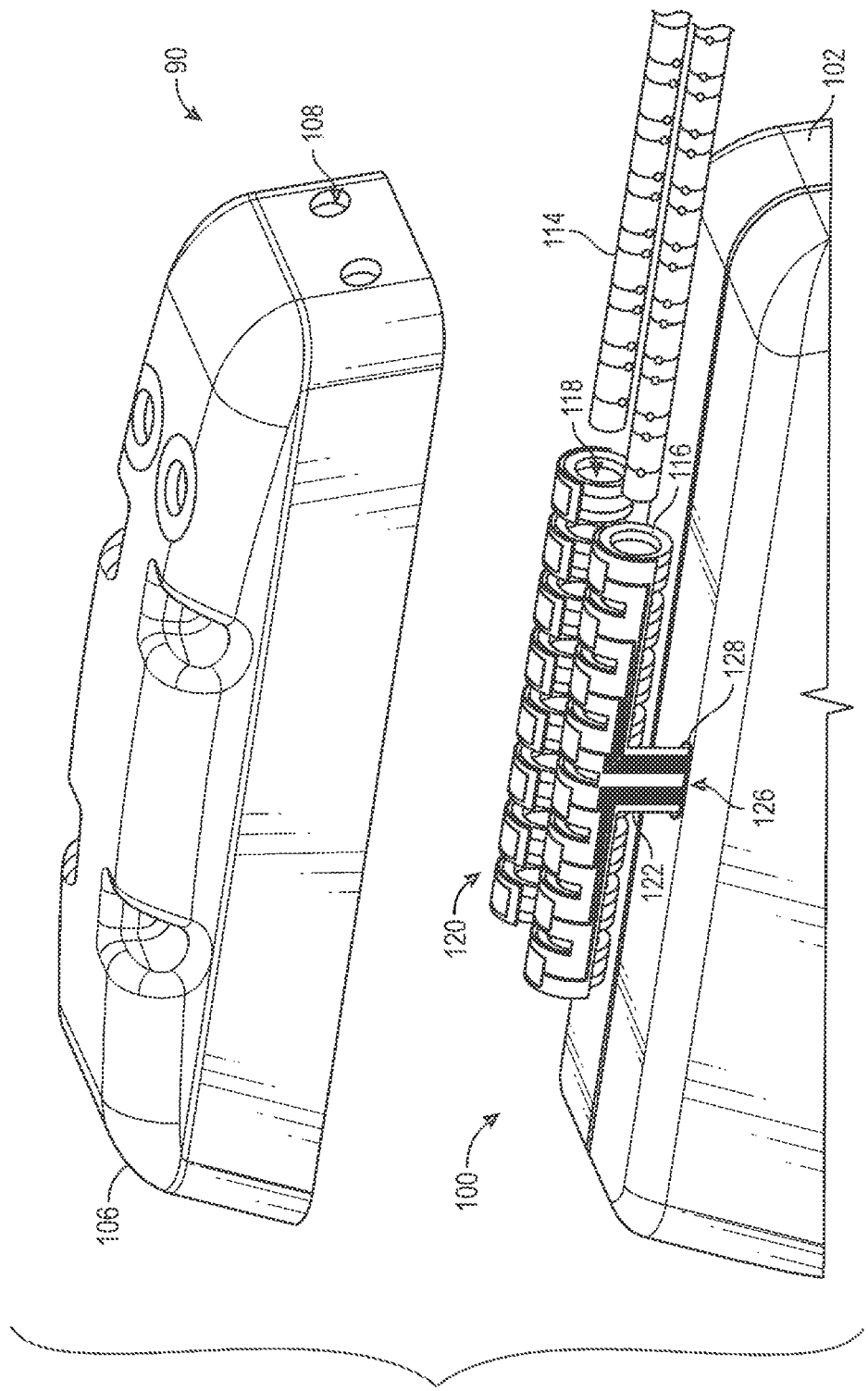
FIG. 16 is another example IED incorporating a set of LCP thin film feedthroughs. The header cover of the IED is shown disconnected from the housing for clarity. A hermetic junction of the LCP thin film feedthroughs comprises a thin metal flange.
Figure 17:
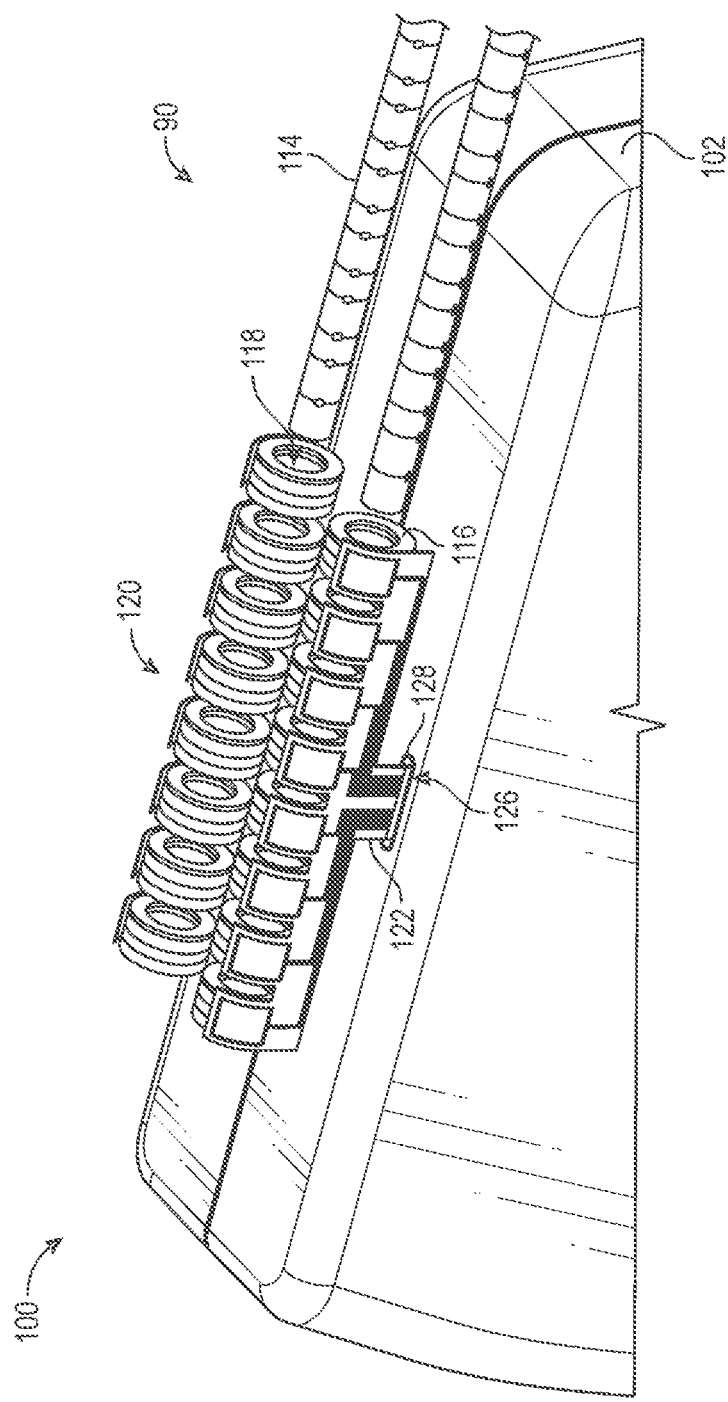
FIG. 17 is another example IED incorporating a set of glass thin film feedthroughs. A hermetic junction of the glass thin film feedthroughs comprises a thin metal flange.
Figure 18:
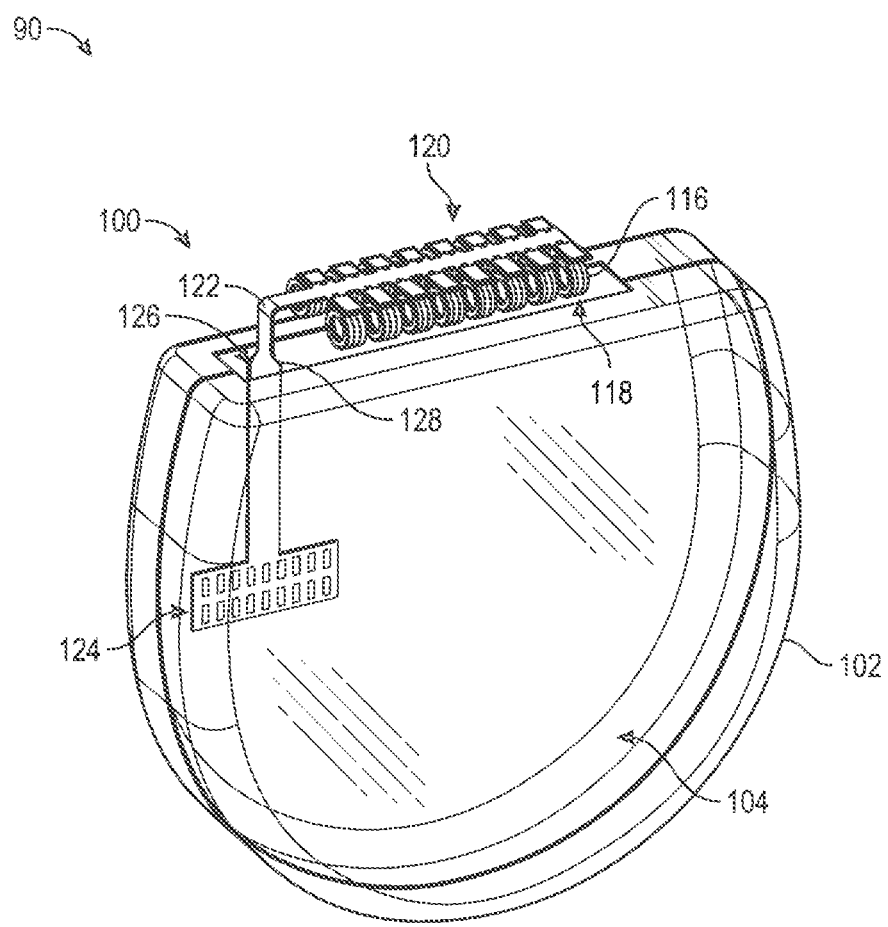
FIG. 18 is another example IED having a thin film feedthrough. A housing of the IED is shown transparent for clarity.

As can be understood through a comparison of FIGS. 4-5 with FIGS. 13-14, the thin film feedthrough 100 may have a variety of geometries and sizes depending on an overall configuration of the implantable electronic system 70 and the various connection junctions with internal and external electronic components. For example, the thin film feedthrough 100 of FIGS. 4-5 has an elongated geometry configured for a single connection junction with the implantable lead 80. Conversely, the thin film feedthrough 100 of FIGS. 13-14 has compact geometry that may be configured for a dual connection junction with the implantable lead 80. An example of this dual connection junction is shown in FIGS. 15-17, which includes a set of the thin film feedthroughs 100, each configured to electrically connect to a corresponding implantable lead 80. This configuration provides two eight channel electrical pathways, as opposed to the single sixteen channel electrical pathway configuration of FIGS. 2-5. FIG. 18 shows the thin film feedthrough 100 configured for a single connection junction similar to the example shown in FIGS. 2-5, with a difference being a geometry of the internal connection assembly 124, customized for particular internal electrical components within the hermetic environment 104.

Figure 20:
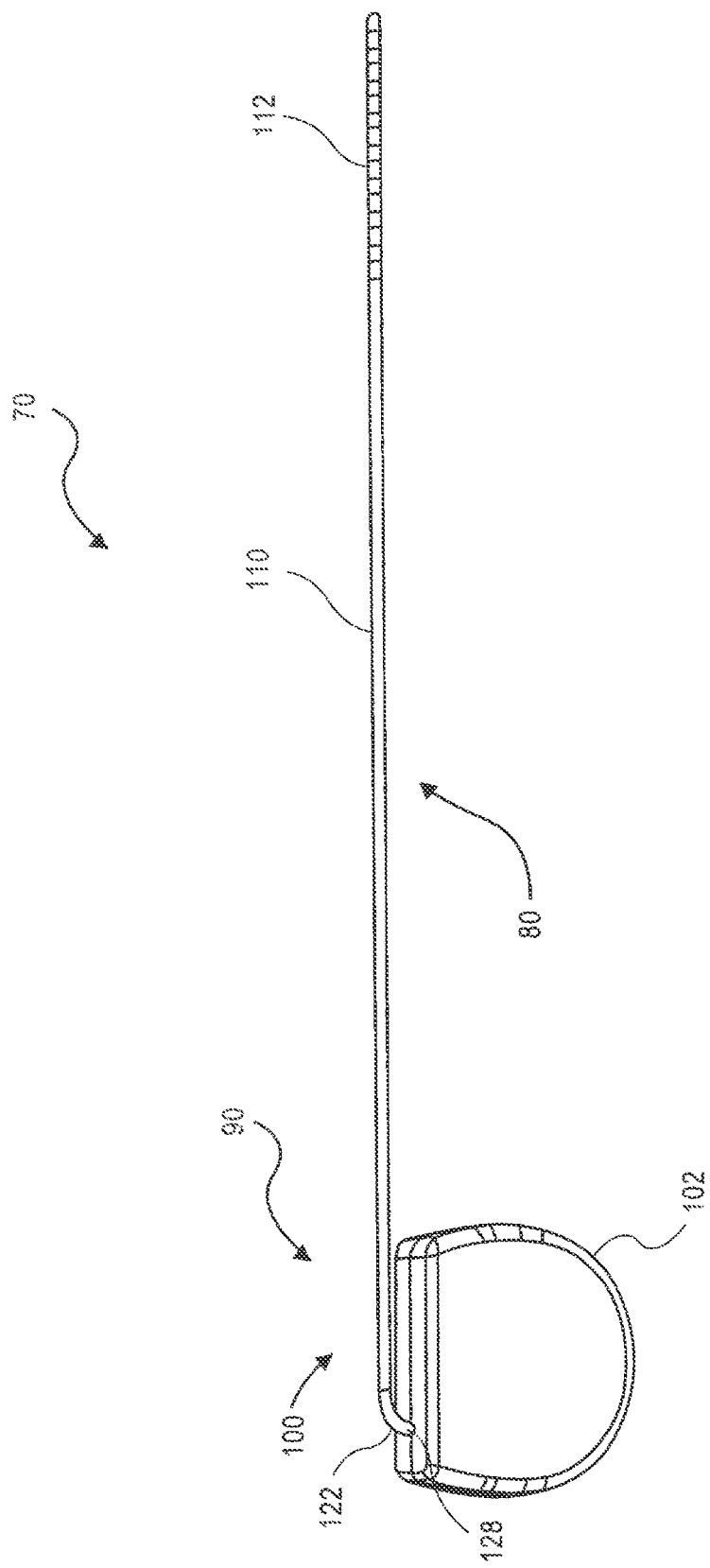
FIG. 20 shows an example implantable electronic system having a thin film circuit comprising an integral feedthrough and lead.

A geometry of the thin film feedthrough 100 may be further correlated with a geometry of the feedthrough port 126, as described herein. For example, as shown in the examples of FIGS. 2-3 and 20, the feedthrough port 126 may be disposed near an edge of the housing 102 where the thin film feedthrough 100 has the elongated geometry. Conversely, the feedthrough ports 126 may be disposed relative to each other near a center of the housing 102 where the thin film feedthrough 100 has the compact geometry, as shown in FIGS. 15-17.

In addition to the design of the feedthrough port 126 varying depending on the design of the thin film feedthrough 100, the hermetic junction 128 may vary accordingly. For example, turning to FIG. 15, in one implementation, the thin film feedthroughs 100 are each made using LCP, as described herein, and the hermetic junction 128 comprises an LCP flange. Similarly, the implementation of the thin film feedthroughs 100 shown in FIG. 16 may be LCP thin film feedthroughs with the hermetic junction 128 comprising a thin metal flange. The thin film feedthroughs 100 of FIG. 17 may be, for example, glass thin film feedthroughs with the hermetic junction 128 comprising a thin metal flange.

Figure 19:
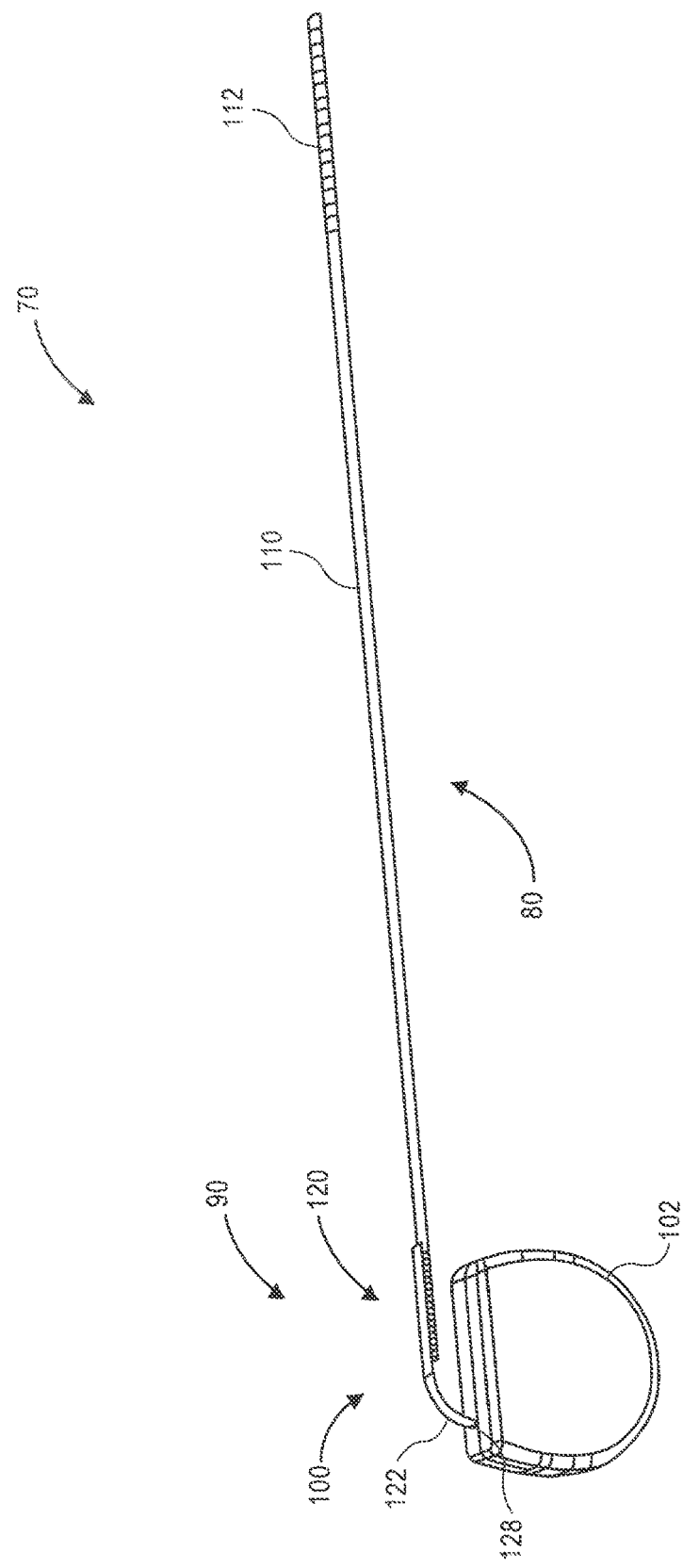
FIG. 19 illustrates an example implantable electronic system with a connection junction electrically connecting a thin film lead to a thin film feedthrough of an IED.

As described herein, in one implementation, the thin film feedthrough 100 may be a tip-to-tall flexible circuit having external connectors electrically connected to internal connectors via a feedthrough body, which is sealed with the hermetic junction 128. The internal connectors are configured to electrically connect to internal electrical components housed within the hermetic environment 104 at an internal connection junction. In one implementation, for example as shown in FIG. 19, the external connectors are configured to electrically connect to an external electrical component, such as the implantable lead 80, at an external connection junction. In another implementation, as shown in FIG. 20, the external connectors are configured to deliver electrical signals between the internal electrical components and tissue within the target location of the patient 10. Stated differently, the thin film feedthrough 100 may be a full-tip-to-tail flexible circuit comprising an integral feedthrough and lead.

Various other modifications and additions can be made to the exemplary implementations discussed without departing from the spirit and scope of the presently disclosed technology. For example, while the embodiments described above refer to particular features, the scope of this disclosure also includes implementations having different combinations of features and implementations that do not include all of the described features. Accordingly, the scope of the presently disclosed technology is intended to embrace all such alternatives, modifications, and variations together with all equivalents thereof.

What is claimed is:

1. An implantable electronic device comprising:
   a housing enclosing one or more internal electronic components within a hermetic environment;
   a feedthrough port defined in a wall of the housing;
   a thin film feedthrough having a feedthrough body extending through the feedthrough port, the feedthrough body providing one or more electrical pathways between external contacts and internal contacts, the external contacts disclosed outside the hermetic environment and the internal contacts electrically connected to the one or more internal electronic components at an internal connection junction; and
   a hermetic junction disposed in the feedthrough port isolating the thin film feedthrough from the housing;
   wherein the thin film feedthrough is manufactured by:
      forming an insulator having an inner surface and an outer surface;
      fabricating a layer of conductive traces on the inner surface of the insulator using biocompatible metallization, the layer of conductive traces defining a trace pattern;
      applying an insulating layer over the layer of conductive traces with intimate contact between the inner surface of the insulator and an inner surface of the insulating layer outside of the trace pattern, the insulating layer having an outer surface opposite the inner surface; and
      fabricating an external connection array and an internal connection array on at least one of the outer surface of the insulator or the outer surface of the insulating layer, the external connection array and the internal connection array in electrical communication with the layer of conductive traces to form the thin film feedthrough.

2. The implantable electronic device of claim 1, wherein the external contacts are electrically connected to one or more external electrical components at an external connection junction.

3. The implantable electronic device of claim 2, wherein the one or more external electrical components include an implantable lead, the external contacts are electrically connected to a terminal end of the implantable lead at the external connection junction.

4. The implantable electronic device of claim 1, wherein the insulator is made from at least one of: polyimide, glass, ceramic, liquid crystal polymer, organic thermoplastic polymer, inorganic material, non-conductive oxide, or thermoset polymer.

5. The implantable electronic device of claim 1, wherein the trace pattern is defined through at least one of: ablation, etching, resist printing, conductive printing, insulative impregnation, insulative implantation, electroplating, electroless deposition, or through-mask plating.

6. The implantable electronic device of claim 1, wherein the insulating layer is applied through at least one of: extrusion, coating, casting, deposition, lamination, or printing.

7. The implantable electronic device of claim 1, wherein the layer of conductive traces are made from one or more layers of noble metal.

8. The implantable electronic device of claim 1, wherein one or more vies are formed in at least one of the outer surface of the shaped insulator or the outer surface of the insulating layer, the one or more vias filled with conductive material to establish the electrical communication between the electrode array and the layer of conductive traces.

9. The implantable electronic device of claim 1, wherein the thin film feedthrough is fabricated using at least one of a plated through hole integration process, a sequential metal integration process, or a glass feedthrough process.

10. An implantable electronic device comprising:
a housing enclosing one or more internal electronic components within a hermetic environment;
a feedthrough port defined in a wall of the housing;
a thin film feedthrough having a feedthrough body extending through the feedthrough port, the feedthrough body providing one or more electrical pathways between external contacts and internal contacts, the external contacts disposed outside the hermetic environment and the internal contacts electrically connected to the one or more internal electronic components at an internal connection junction; and
a hermetic junction disposed in the feedthrough port isolating the thin film feedthrough from the housing;
wherein the thin film feedthrough further includes a substrate, an interconnect layer deposited over the substrate, and a passivation layer deposited over the interconnect layer.

11. The implantable electronic device of claim 10, wherein the substrate is made from at least one of a liquid crystal polymer, glass, or ceramic.

12. The implantable electronic device of claim 10, wherein the passivation layer is made from at least one of a liquid crystal polymer, silicon dioxide, or silicon nitride.

13. The implantable electronic device of claim 10, wherein the substrate has a two-dimensional profile shape or a three dimensional profile shape.

14. The implantable electronic device of claim 10, wherein the hermetic junction includes a flange sealed at one or more hermetic interfaces through hermetic sealing, the one or more hermetic interfaces including at least one of a first hermetic sealing interface between the flange and the feedthrough body or a second hermetic sealing interface between the flange and the housing.

15. The implantable electronic device of claim 14, wherein the flange is made from at least one of liquid crystal polymer, metal, or glass.

16. The implantable electronic device of claim 14, wherein the flange includes a neck extending between a body and a retaining lip, the body including proximal body surface extending between a first set of body surfaces and a second set of body surfaces, the retaining lip tapering in thickness from a proximal retaining surface to a distal retaining surface, a slot extending through the flange from the proximal body surface to the distal retaining surface, the hermetic seating created by reflowing a material of the flange at the one or more hermetic interfaces using localized heat.

17. The implantable electronic device of claim 14, wherein the flange includes a ring body extending between a proximal ring surface and a distal ring surface, the ring body including a slot, the hermetic sealing created by welding the flange at the one or more hermetic interfaces.

18. The implantable electronic device of claim 10, wherein the hermetic junction includes a glass bead applied around the feedthrough port between the feedthrough body and the housing, the hermetic junction including hermetic sealing created by annealing the glass bead.

19. The implantable electronic device of claim 10, wherein the hermetic junction includes an adhesive applied around the feedthrough port between the feedthrough body and the housing, the hermetic junction including hermetic sealing created by curing the adhesive.

20. The implantable electronic device of claim 19, wherein the adhesive is at least one of epoxy or liquid crystal polymer with a solvent.

* * * * *